(12) United States Patent
Ticker

(10) Patent No.: US 11,020,218 B2
(45) Date of Patent: Jun. 1, 2021

(54) TISSUE CAPTURING BONE ANCHOR

(71) Applicant: Conmed Corporation, Utica, NY (US)

(72) Inventor: Jonathan B. Ticker, Brookville, NY (US)

(*) Notice: Subject to any disclaimer, the term of this patent is extended or adjusted under 35 U.S.C. 154(b) by 0 days.

(21) Appl. No.: 16/199,660

(22) Filed: Nov. 26, 2018

(65) Prior Publication Data

US 2019/0117377 A1   Apr. 25, 2019

Related U.S. Application Data

(63) Continuation of application No. 14/774,675, filed as application No. PCT/US2014/002177 on Mar. 7, 2014, now Pat. No. 10,149,751.

(60) Provisional application No. 61/786,168, filed on Mar. 14, 2013.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 17/0485* (2013.01); *A61B 17/0483* (2013.01); *A61B 2017/0409* (2013.01); *A61B 2017/0414* (2013.01); *A61B 2017/0432* (2013.01); *A61B 2017/0438* (2013.01); *A61B 2017/0445* (2013.01); *A61B 2017/0456* (2013.01); *A61F 2002/0835* (2013.01)

(58) Field of Classification Search
CPC .. A61F 2/08; A61F 2/0811; A61F 2002/0835; A61B 17/04; A61B 17/0401; A61B 17/0485; A61B 17/0483; A61B 2017/0409; A61B 2017/0414; A61B 2017/0432
See application file for complete search history.

(56) References Cited

U.S. PATENT DOCUMENTS

| 4,484,570 | A | * | 11/1984 | Sutter | ............... A61B 17/8038 606/282 |
|---|---|---|---|---|---|
| 4,590,928 | A | | 5/1986 | Hunt et al. | |
| 4,738,255 | A | | 4/1988 | Goble et al. | |
| 4,790,304 | A | | 12/1988 | Rosenberg | |
| 4,851,005 | A | | 7/1989 | Hunt et al. | |

(Continued)

FOREIGN PATENT DOCUMENTS

| DE | 19731298 | 11/1999 |
|---|---|---|
| EP | 0270704 | 6/1988 |

(Continued)

OTHER PUBLICATIONS

"Executive Interview: Chris Fair, Chief Operations Officer; Ken Gall, Ph.D., Director Chief Techical Officer, MedShape Solutions, Inc.," Orthopreneur, pp. 22-25, Jan./Feb. 2010.

(Continued)

*Primary Examiner* — George J Ulsh

(57) ABSTRACT

A bone anchor configured for use in anchoring an implanting portion to an anchor point. A bone anchor can be of particular use in anchoring soft tissue to a bone. A bone anchor can have a wire loop and a suture. The wire loop of the bone anchor can be configured to capture a suture and to pull a portion of the suture through a hole in the anchor body aiding in anchoring an item, such as tissue to a bone. Methods of using the bone anchor with a suture and a wire loop to attach an item are disclosed

7 Claims, 36 Drawing Sheets

(56) References Cited

U.S. PATENT DOCUMENTS

| | | |
|---|---|---|
| 4,870,957 A | 10/1989 | Goble et al. |
| 4,960,420 A | 10/1990 | Goble et al. |
| 4,988,351 A | 1/1991 | Paulos et al. |
| 5,037,422 A | 8/1991 | Hayhurst et al. |
| 5,161,916 A | 11/1992 | White et al. |
| 5,167,665 A | 12/1992 | McKinney |
| 5,176,682 A | 1/1993 | Chow |
| 5,192,303 A | 3/1993 | Gatturna et al. |
| 5,197,983 A | 3/1993 | Berman et al. |
| 5,209,756 A | 5/1993 | Seedhom et al. |
| 5,222,963 A | 6/1993 | Brinkerhoff et al. |
| 5,224,946 A | 7/1993 | Hayhurst et al. |
| 5,246,443 A | 9/1993 | Mai |
| 5,268,001 A | 12/1993 | Nicholson et al. |
| 5,326,205 A | 7/1994 | Anspach, Jr. et al. |
| 5,336,240 A | 8/1994 | Metzler et al. |
| 5,354,298 A | 10/1994 | Lee et al. |
| 5,372,599 A | 12/1994 | Martins |
| 5,380,334 A | 1/1995 | Torrie et al. |
| 5,397,356 A | 3/1995 | Goble et al. |
| 5,417,691 A | 5/1995 | Hayhurst |
| 5,417,712 A | 5/1995 | Whittaker et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,500,001 A | 3/1996 | Trott |
| 5,501,683 A | 3/1996 | Trott |
| 5,501,695 A * | 3/1996 | Anspach, Jr. ...... A61B 17/0401 411/34 |
| 5,505,735 A | 4/1996 | Li |
| 5,522,844 A | 6/1996 | Johnson |
| 5,522,845 A | 6/1996 | Wenstrom, Jr. |
| 5,522,846 A | 6/1996 | Bonutti |
| 5,545,180 A | 8/1996 | Le et al. |
| 5,554,171 A | 9/1996 | Gatturna et al. |
| 5,569,306 A | 10/1996 | Thal |
| 5,601,557 A | 2/1997 | Hayhurst |
| 5,618,314 A | 4/1997 | Harwin et al. |
| 5,628,751 A | 5/1997 | Sander et al. |
| 5,632,748 A | 5/1997 | Beck, Jr. et al. |
| 5,643,266 A | 7/1997 | Li |
| 5,643,274 A | 7/1997 | Sander et al. |
| 5,643,321 A | 7/1997 | McDevitt |
| 5,645,589 A | 7/1997 | Li |
| 5,649,963 A | 7/1997 | McDevitt |
| 5,690,649 A | 11/1997 | Li |
| 5,702,215 A | 12/1997 | Li |
| 5,707,395 A | 1/1998 | Li |
| 5,713,903 A | 2/1998 | Sander et al. |
| 5,718,717 A | 2/1998 | Bonutti |
| 5,720,753 A | 2/1998 | Sander et al. |
| 5,725,557 A | 3/1998 | Gatturna et al. |
| 5,733,306 A | 3/1998 | Bonutti |
| 5,741,282 A | 4/1998 | Anspach, III et al. |
| 5,749,899 A | 5/1998 | Bardin |
| 5,782,865 A | 7/1998 | Grotz |
| 5,797,963 A | 8/1998 | McDevitt |
| 5,814,071 A | 9/1998 | McDevitt et al. |
| 5,814,072 A | 9/1998 | Bonutti |
| 5,849,004 A | 12/1998 | Bramlet |
| 5,891,168 A | 4/1999 | Thal |
| 36,289 A | 8/1999 | Le et al. |
| RE36,289 E | 8/1999 | Le et al. |
| 5,948,000 A | 9/1999 | Larsen et al. |
| 5,948,002 A | 9/1999 | Bonutti |
| 5,957,953 A | 9/1999 | DiPoto et al. |
| 5,964,764 A | 10/1999 | West, Jr. et al. |
| 5,968,078 A | 10/1999 | Grotz |
| 5,980,558 A | 11/1999 | Wiley |
| 6,007,566 A | 12/1999 | Wenstrom, Jr. |
| 6,022,373 A | 2/2000 | Li |
| 6,024,758 A | 2/2000 | Thal |
| 6,063,037 A | 5/2000 | Mittermeier et al. |
| 6,077,292 A | 6/2000 | Bonutti |
| 6,086,591 A | 7/2000 | Bojarski |
| 6,146,406 A | 11/2000 | Shluzas et al. |
| 6,149,669 A | 11/2000 | Li |
| 6,203,565 B1 | 3/2001 | Bonutti et al. |
| 6,241,732 B1 | 6/2001 | Overaker et al. |
| 6,287,324 B1 | 9/2001 | Yarnitsky et al. |
| 6,312,448 B1 | 11/2001 | Bonutti |
| 6,319,269 B1 | 11/2001 | Li |
| 6,328,758 B1 | 12/2001 | Tornier et al. |
| 6,464,713 B2 | 10/2002 | Bonutti |
| 37,963 A1 | 1/2003 | Thal |
| RE37,963 E | 1/2003 | Thal |
| 6,540,770 B1 | 4/2003 | Tornier et al. |
| 6,544,281 B2 | 4/2003 | Elattrache et al. |
| 6,547,800 B2 | 4/2003 | Foerster et al. |
| 6,554,862 B2 | 4/2003 | Hays et al. |
| 6,562,071 B2 | 5/2003 | Jarvinen |
| 6,582,453 B1 | 6/2003 | Tran et al. |
| 6,585,730 B1 | 7/2003 | Foerster |
| 6,616,694 B1 | 9/2003 | Hart |
| 6,632,224 B2 | 10/2003 | Cachia et al. |
| 6,635,073 B2 | 10/2003 | Bonutti |
| 6,641,597 B2 | 11/2003 | Burkhart et al. |
| 6,648,890 B2 | 11/2003 | Culbert et al. |
| 6,652,561 B1 | 11/2003 | Tran |
| 6,656,183 B2 | 12/2003 | Colleran et al. |
| 6,660,022 B1 | 12/2003 | Li et al. |
| 6,660,023 B2 | 12/2003 | McDevitt et al. |
| 6,673,094 B1 | 1/2004 | McDevitt et al. |
| 6,689,135 B2 | 2/2004 | Enayati |
| 6,692,516 B2 | 2/2004 | West, Jr. et al. |
| 6,746,483 B1 | 6/2004 | Bojarski et al. |
| 6,770,076 B2 | 8/2004 | Foerster |
| 6,840,953 B2 | 1/2005 | Martinek |
| 6,846,313 B1 | 1/2005 | Rogers et al. |
| 6,887,271 B2 | 5/2005 | Justin et al. |
| 6,890,354 B2 | 5/2005 | Steiner et al. |
| 6,932,834 B2 | 8/2005 | Lizardi et al. |
| 7,008,451 B2 | 3/2006 | Justin et al. |
| 7,037,324 B2 | 5/2006 | Martinek |
| 7,052,498 B2 | 5/2006 | Levy et al. |
| 7,087,073 B2 | 8/2006 | Bonutti |
| 7,144,413 B2 | 12/2006 | Wilford et al. |
| 7,144,415 B2 | 12/2006 | Del Rio et al. |
| 7,201,754 B2 | 4/2007 | Stewart et al. |
| 7,226,469 B2 | 6/2007 | Benavitz et al. |
| 7,235,100 B2 | 6/2007 | Martinek |
| 7,309,346 B2 | 12/2007 | Martinek |
| 7,309,355 B2 | 12/2007 | Donnelly et al. |
| 7,329,272 B2 | 2/2008 | Burkhart et al. |
| 7,329,281 B2 | 2/2008 | Hays et al. |
| 7,381,213 B2 | 6/2008 | Lizardi |
| 7,520,898 B2 | 4/2009 | Re et al. |
| 7,556,640 B2 | 7/2009 | Foerster |
| 7,572,283 B1 | 8/2009 | Meridew |
| 7,588,586 B2 | 9/2009 | Whittaker |
| 7,611,521 B2 | 11/2009 | Lubbers et al. |
| 605,763 A1 | 12/2009 | Griffiths, III et al. |
| D605,763 S | 12/2009 | Griffis, III et al. |
| 7,651,528 B2 | 1/2010 | Montgomery et al. |
| 7,674,274 B2 | 3/2010 | Foerster et al. |
| 7,699,893 B2 | 4/2010 | Donnelly et al. |
| 7,713,285 B1 | 5/2010 | Stone et al. |
| 7,828,802 B2 | 11/2010 | Levy et al. |
| 7,833,254 B2 | 11/2010 | Celli et al. |
| 7,846,162 B2 | 12/2010 | Nelson et al. |
| 7,862,612 B2 | 1/2011 | Re et al. |
| 7,879,094 B2 | 2/2011 | Baird et al. |
| 7,896,901 B2 | 3/2011 | Whittaker |
| 7,901,456 B2 | 3/2011 | Justin et al. |
| 7,918,879 B2 | 4/2011 | Yeung et al. |
| 7,967,861 B2 | 6/2011 | Montgomery et al. |
| 7,993,368 B2 | 8/2011 | Gambale et al. |
| 8,048,158 B2 | 11/2011 | Hays et al. |
| 8,062,334 B2 | 11/2011 | Green et al. |
| 8,069,858 B2 | 12/2011 | Gall |
| 8,080,044 B2 | 12/2011 | Biedermann et al. |
| 8,128,663 B2 | 3/2012 | Zucherman et al. |
| 8,162,942 B2 | 4/2012 | Coati et al. |

(56) References Cited

U.S. PATENT DOCUMENTS

| | | | |
|---|---|---|---|
| 8,162,978 B2 | 4/2012 | Lombardo et al. | |
| 8,192,490 B2 | 6/2012 | Baird et al. | |
| 8,221,479 B2 | 7/2012 | Glazer et al. | |
| 8,317,863 B2 | 11/2012 | Cauldwell et al. | |
| 8,414,647 B2 | 4/2013 | Baird et al. | |
| 8,430,933 B2 | 4/2013 | Gall | |
| 8,435,294 B2 | 5/2013 | Montgomery et al. | |
| 8,523,902 B2 | 9/2013 | Heaven et al. | |
| 8,545,535 B2 | 10/2013 | Hirotsuka et al. | |
| 8,652,208 B2 | 2/2014 | Baird et al. | |
| 8,747,469 B2 | 6/2014 | Wang et al. | |
| 8,906,060 B2 | 12/2014 | Hart | |
| 8,986,345 B2 | 3/2015 | Denham et al. | |
| 9,044,313 B2 | 6/2015 | Heaven | |
| 9,155,574 B2 | 10/2015 | Saravia et al. | |
| 9,510,816 B2 | 12/2016 | McDevitt et al. | |
| 9,706,984 B2 | 7/2017 | Heaven et al. | |
| 9,826,970 B2 | 11/2017 | Heaven et al. | |
| 9,968,349 B2 | 5/2018 | Heaven et al. | |
| 10,076,377 B2 * | 9/2018 | Bonutti | A61F 2/0805 |
| 2003/0100903 A1 | 5/2003 | Cooper | |
| 2003/0195564 A1 | 10/2003 | Tran et al. | |
| 2004/0010287 A1 | 1/2004 | Bonutti | |
| 2004/0098053 A1 | 5/2004 | Tran | |
| 2004/0138683 A1 | 7/2004 | Shelton et al. | |
| 2004/0230194 A1 * | 11/2004 | Urbanski | A61B 17/0642 |
| | | | 606/68 |
| 2006/0229617 A1 | 10/2006 | Meller et al. | |
| 2006/0282081 A1 | 12/2006 | Fanton et al. | |
| 2007/0027477 A1 | 2/2007 | Chudik | |
| 2007/0055242 A1 * | 3/2007 | Bailly | A61B 17/7037 |
| | | | 606/266 |
| 2008/0195221 A1 | 8/2008 | Howald et al. | |
| 2008/0221624 A1 | 9/2008 | Gooch | |
| 2009/0030516 A1 | 1/2009 | Imbert | |
| 2009/0043342 A1 | 2/2009 | Freedland | |
| 2009/0149884 A1 | 6/2009 | Snyder et al. | |
| 2009/0187216 A1 | 7/2009 | Schmieding et al. | |
| 2010/0033188 A1 | 2/2010 | Rieth | |
| 2010/0198258 A1 * | 8/2010 | Heaven | A61B 17/0401 |
| | | | 606/232 |
| 2012/0130492 A1 * | 5/2012 | Eggli | A61F 2/08 |
| | | | 623/13.14 |
| 2012/0239038 A1 | 9/2012 | Saravia et al. | |
| 2014/0046369 A1 * | 2/2014 | Heaven | A61B 17/0401 |
| | | | 606/232 |

FOREIGN PATENT DOCUMENTS

| | | |
|---|---|---|
| EP | 0241240 | 9/1989 |
| EP | 0409364 | 3/1991 |
| EP | 0504915 | 9/1992 |
| EP | 0574707 | 12/1993 |
| EP | 0673624 | 11/1995 |
| EP | 1348380 | 10/2003 |
| EP | 2266469 | 12/2010 |
| EP | 2488118 | 8/2012 |
| FR | 2671717 | 7/1992 |
| WO | 1995/015726 | 6/1995 |
| WO | 1997/007741 | 3/1997 |
| WO | 2002/032345 | 4/2002 |
| WO | 2003/105700 | 12/2003 |
| WO | 2005070314 | 8/2005 |
| WO | 2006/055823 | 5/2006 |
| WO | 2008/073588 | 6/2008 |
| WO | 2009/154781 | 12/2009 |
| WO | 2009154781 | 12/2009 |
| WO | 2010/088561 | 8/2010 |
| WO | 2011/046982 | 4/2011 |
| WO | 2012/093961 | 7/2012 |
| WO | 2012/148693 | 11/2012 |
| WO | 2012093961 | 12/2012 |
| WO | 2015/059582 | 4/2015 |

OTHER PUBLICATIONS

"Scope This Out: A Technical Pearls Newsletter for Arthroscopists," Spring 2010, pp. 1-8, vol. 12, No. 1, Arthrex, Inc.

Boileau et al., "Arthroscopic Biceps Tenodesis: A New Technique Using Bioabsorbable Interference Screw Fixation," J Arthrosc Related Surgery, vol. 18, No. 9, (Nov.-Dec. 2002), 1002-1012.

Extended European Search Report dated Feb. 27, 2017, PCT/US2014/022014; 10 pages.

Extended European Search Report dated Oct. 13, 2016, PCT/US2014/021774; 7 pages.

Green et al., "Arthroscopic Versus Open Bankart Procedures: A Comparison of Early Morbidity and Complications," The Journal of Arthroscopic and Related Surgery, col. 9, No. 4, 371-374 (1993).

Hecker et al., "Pull-out strength of suture anchors for rotator cuff and Bankart lesion repairs," The American Journal of Sports Medicine, vol. 21, No. 6, 874-879 (1993).

International Preliminary Report on Patentability dated Apr. 7, 2015 for International Application No. PCT/US2013/063275, filed Oct. 3, 2013.

International Preliminary Report on Patentability dated Aug. 2, 2011 for International Application No. PCT/US2010/022661, filed Jan. 29, 2010.

International Search Report and written Opinion dated Aug. 6, 2012, for International Patent Application No. PCT/US2012/033392, filed Apr. 12, 2012.

International Search Report and Written Opinion dated Dec. 9, 2010, for International Patent Application No. PCT/US2010/052398, filed Oct. 12, 2010.

International Search Report and Written Opinion dated Feb. 3, 2014 for International Application No. PCT/US2013/063275, filed Oct. 3, 2013.

International Search Report and Written Opinion dated Jan. 18, 2013 for International Application No. PCT/US2012/058786, filed Oct. 4, 2012.

Richards et al., "A Biomechanical Analysis of Two Biceps Tenodesis Fixation Techniques," Arthroscopy: The Journal of Arthroscopic and Related Surgery, vol. 21, No. 7, 2005: pp. 861-866.

Shall et al., "Soft Tissue Reconstruction in the Shoulder," The American Journal of Sports Medicine, vol. 22, No. 5, 715-718 (1994).

Sherman et al., "The long-term followup of primary anterior cruciate ligament repair," The American Journal of Sports Medicine, vol. 19, No. 3, 243-255 (1991).

USS Sports Medicine presents POLYSORB 3mm Soft Tissue Anchor System, US Surgical Corp., Date of Publication unknown; 2 pages.

Whipple et al., "A Technique for Arthroscopic Anterior Cruciate Ligament Repair," Clinics in Sports Medicine, vol. 10, No. 3, 463-468 (1991).

Yakacki et al., "The Design and Pullout Strength of a Novel Shape-Memory PEEK Suture Anchor," 56th Annual Meeting of the Orthopaedic Research Society, Poster No. 1801 presented on approximately Mar. 1, 2010.

International Search Report and Written Opinion dated Aug. 19, 2010 for International Application No. PCT/US2010/022661 filed Jan. 29, 2010 pp. 1-23.

International Search Report and Written Opinion dated Aug. 19, 2010 Feb. 3, 2014 for International Application No. PCT/US2013/063275 filed Oct. 3, 2013, pp. 1-10.

* cited by examiner

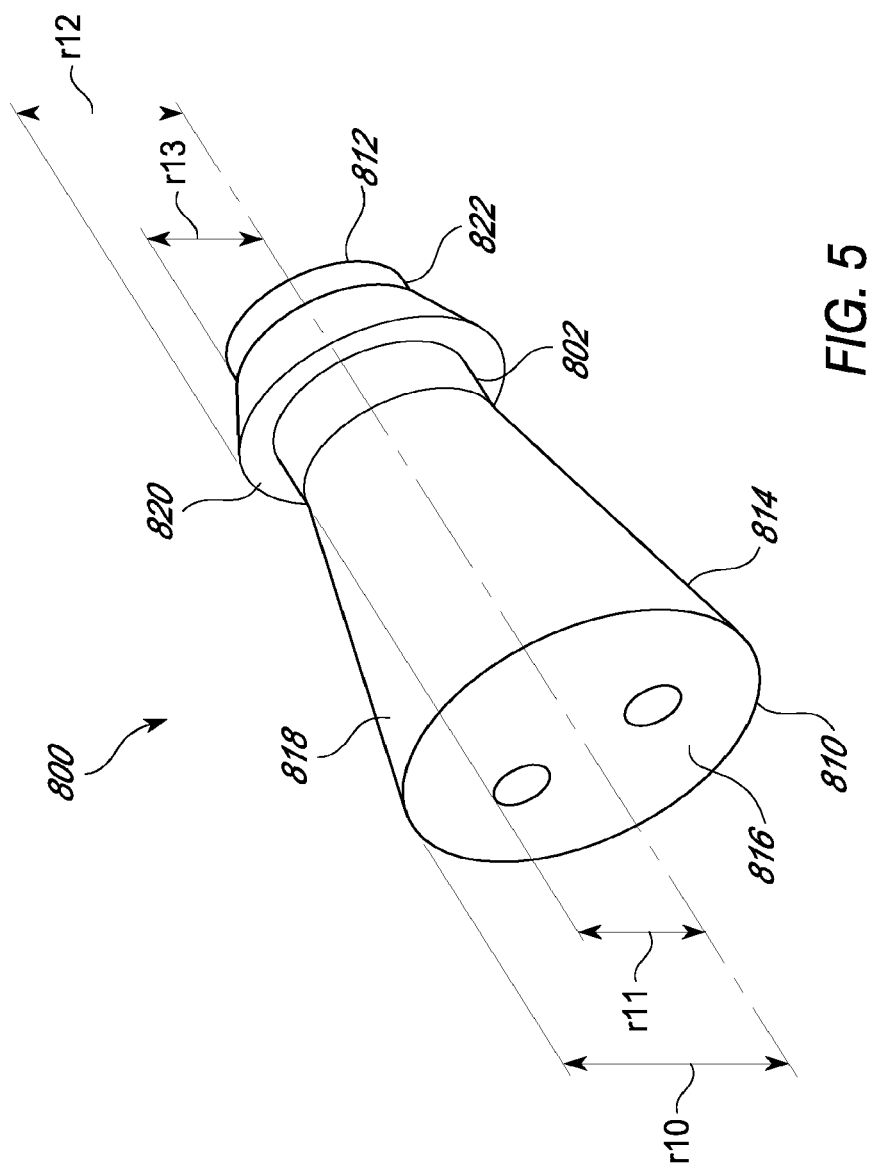

TISSUE CAPTURING BONE ANCHOR

INCORPORATION BY REFERENCE TO ANY PRIORITY APPLICATION

This application is a continuation of U.S. patent application Ser. No. 14/774,675, filed Sep. 10, 2015, which claims priority to 371 National Stage Entry Application Serial No. PCT/US2014/021774, filed Mar. 7, 2014, which claims the benefit and priority of U.S. Provisional Application Ser. No. 61/786,168, filed Mar. 14, 2013, which is hereby incorporated by reference in its entirety.

BACKGROUND OF THE INVENTION

Field of the Invention

The present invention relates to medical devices and procedures. More particularly, the present invention relates to devices and methods for securing soft tissue to a rigid material such as bone.

Description of the Related Art

There are several medical procedures where a surgeon needs to attach soft tissue such as tendons or other soft connective tissue to bone. One common example is a biceps tenodesis, a surgical procedure usually performed for the treatment of biceps tendonitis of the shoulder. A biceps tenodesis may be performed as an isolated procedure, but more often is part of a larger shoulder surgery such as a rotator cuff repair.

The biceps tendon connects the biceps muscle to the bone. The tendon passes from the muscle to the shoulder joint. Patients with biceps tendon problems may have a detachment of the biceps tendon from the radial tuberosity, for example, or they may have inflammation and irritation of the biceps tendon itself. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

To perform a biceps tenodesis repair, typically a surgical procedure is used and requires the multiple steps of externalizing the tendon, whip stitching it, threading suture through a tenodesis screw, drilling the necessary bone hole and anchor insertion via screwing it in. This is a difficult procedure arthroscopically. Systems recently brought to market still require multiple steps and tools

SUMMARY OF THE INVENTION

Disclosed herein are various embodiments of a bone anchor that may address the aforementioned needs. A bone anchor includes, for example, an expandable anchor body, an expander, and a retractable suture grabber, where the expander comprises at least one expansion portion and a first opening in the distal end of the expander, and the retractable suture grabber extends through the first opening. In some embodiments, the expander is displaceable between a first position relative to the anchor body and a second position relative to the anchor body, wherein the expansion portion is configured to expand the anchor body when the expander is in the second position.

In some embodiments, a bone anchor includes, for example, a retractable suture grabber comprising a wire loop. In other embodiments two limbs of the wire loop extend through the expander and out of a proximal end of the expander.

Other embodiments of a bone anchor include, for example, an expander with a first opening and a second opening in the distal end of the expander, where a suture extends through the second opening. In further embodiments, the suture also extends through the expander and out the proximal end of the expander. In some embodiments of a bone anchor, the suture extends through the first opening of the expander. In further embodiments, the suture further extends through the expander and out the proximal end of the expander. In some embodiments, at least one opening is aligned along an axis of the expander. In some embodiments, at least one opening is offset from an axis of the expander.

Some embodiments relate to an anchor/inserter assembly. This anchor/inserter assembly includes, for example, a bone anchor according to all of the disclosed embodiments and an insertion tool coupled to the disclosed bone anchor. Some embodiment of the anchor/tissue assembly include a retractable suture grabber comprising a wire loop and two limbs of the wire loop extending through the expander, out of a proximal end of the expander, and through an axial passage in the insertion tool. Some embodiments of the anchor/tissue assembly include an expander comprising a second opening in the distal end of the expander and a suture extending through the second opening, where a first limb of the suture extends through the expander, out of a proximal end of the expander, and through an axial passage in the insertion tool. A further embodiment includes a second limb of the suture extending along a side of the insertion tool. Still a further embodiment includes the second limb of the suture being secured to the inserter handle.

Some embodiments relate to a method of attaching soft tissue to a bone anchor comprising inserting the bone anchor according to all of the disclosed embodiments into a patient through a first arthroscopic port, pulling the suture grabber out of the patient through a second arthroscopic port, passing a suture around soft tissue, pulling at least a first limb of the suture out of the patient through the second arthroscopic port, engaging the suture with the suture grabber, and retracting the suture grabber through the first opening in the distal end of the expander, thereby pulling the first limb of the suture through the first opening. In some embodiments of the method, the suture grabber comprises a wire loop and engaging the suture with the suture grabber by passing the suture through the wire loop. Further embodiments can include inserting the anchor into the bone after retracting the suture grabber. In some other embodiments, the method includes a second limb of the suture extending through either the first opening or the second opening in the distal end of the expander prior to insertion of the bone anchor. In still other embodiments, the method includes inserting the first limb of the suture through the second arthroscopic port prior to passing it around the soft tissue. In further embodiments, the method comprises the suture grabber being engaged by the first limb and the second limb of the suture and both the first and second limbs of the suture can be pulled through the first opening when the suture grabber is retracted. Another embodiment of the method of attaching soft tissue comprises making a hole in bone. In some embodiments the hole is made with a drill and the bone can be cleared of any soft tissue in the region of the hole.

BRIEF DESCRIPTION OF THE DRAWINGS

FIG. 5 depicts a perspective view of one embodiment of a single piece expander.

DETAILED DESCRIPTION OF THE PREFERRED EMBODIMENT

Figure 1:
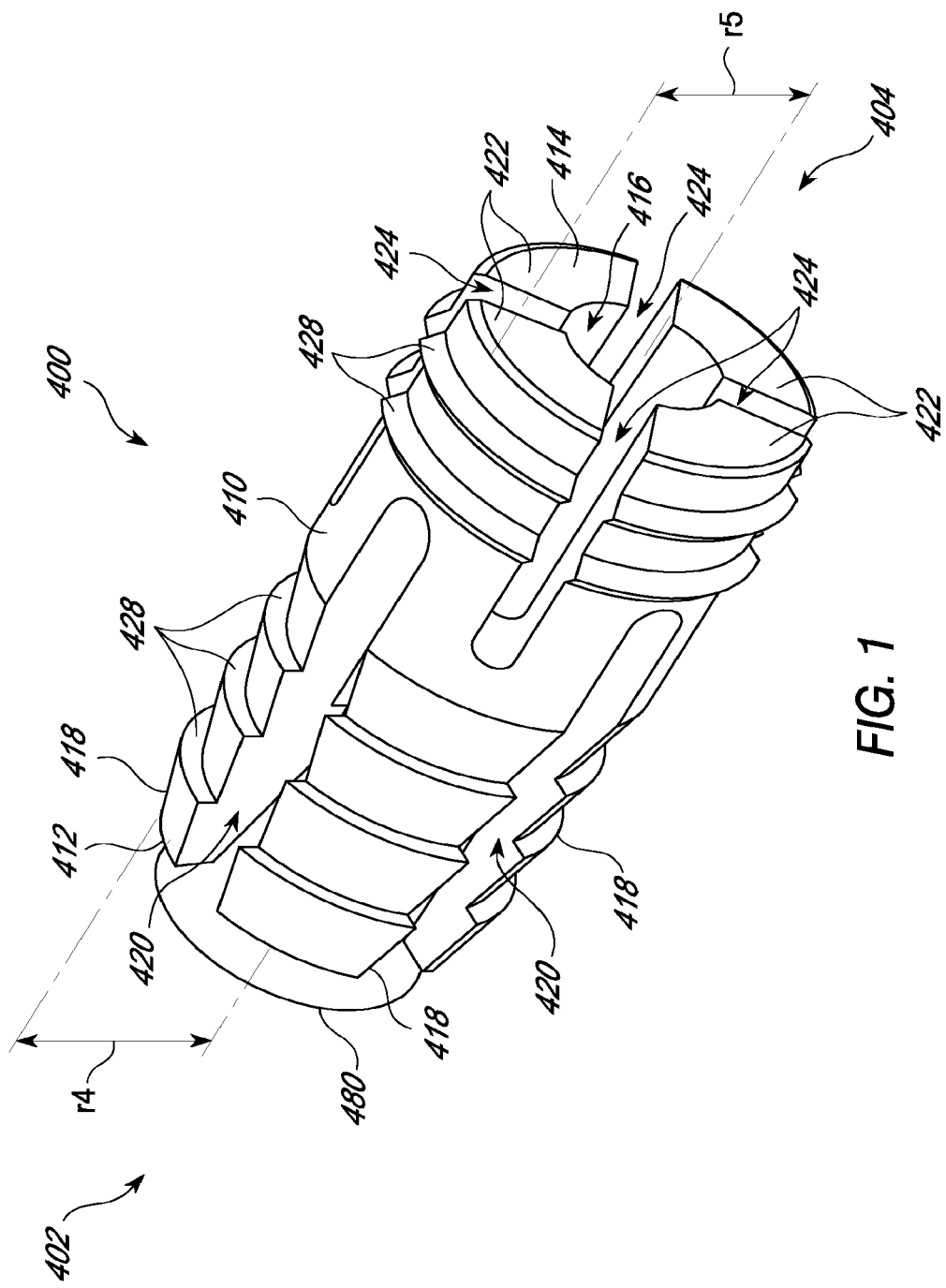
FIG. 1 depicts a perspective view of one embodiment of a bone anchor in an undeployed or unexpanded state.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

The terminology used herein is for the purpose of describing particular embodiments only and is not intended to be limiting of the disclosure. It will be understood by those within the art that if a specific number of an element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

Some embodiments disclosed herein relate generally to anchors for use in anchoring tissue or objects in a body. More specifically, some embodiments disclosed herein relate generally to anchors for use in anchoring soft tissue to bone in a body. Some embodiments disclosed herein relate generally to anchors for use in anchoring sutures to a bone in a body. Also some elements relate to individual components and subcomponents of the systems described herein, as well as methods of making and using the same. Some embodiments additionally relate to kits and components used in connection with the anchor. Although the following embodiments refer to the use of an anchor in anchoring tissue, a person of skill in the art will recognize that an anchor can be used to anchor any range of items within a body.

An exemplary bone anchor can include features configured for retention of the desired tissue and features configured for affixing the anchor to the desired anchor point. FIG. 1 depicts a perspective view of one embodiment of an unexpanded dual expansion bone anchor 400 comprising an anchor body 410 and an expander 480. The anchor has a distal end 402 and a proximal end 404.

The anchor body 410 has a first end 412 and a second end 414. In some embodiments, the first end 412 of the anchor body 410 is configured for placement into a hole in a bone. In some embodiments, the anchor 400 is placed in the hole in the bone so that the second end 414 is in closer proximity to the entrance hole into the bone than the first end 412. The anchor 400 depicted in FIG. 4 has a radius at the first end 412 of r4 and a radius at the second end 414 of r5. In some embodiments r4 and r5 are the same. In some embodiments, r4 and r5 are different.

Anchor 400 can be inserted into an anchor point with an insertion tool. In some embodiments, the second end 414 of the anchor body 410 is configured for interaction with a portion of the insertion tool to thereby allow placement of the anchor 400 at the anchor point. In some embodiments, the second end 414 of the anchor body 410 can be configured to abut portions of the insertion tool. The abutting interaction between the anchor body 410 and the insertion tool can facilitate a transfer of forces between the insertion tool and the anchor body 414, which transfer of forces can facilitate anchor insertion and/or result in deployment or expansion of the anchor 400.

The anchor body 410 depicted in FIG. 1 has an axial bore 416. The axial bore 416 can extend partially or entirely through the anchor body 410. In some embodiments, the axial bore 416 can be a first axial bore partially extending along the length of the anchor body 410 and a second axial bore partially extending along the length of the anchor body 410. The axial bore 416 depicted in FIG. 1 extends the entire length of the anchor body 410.

Figure 4:
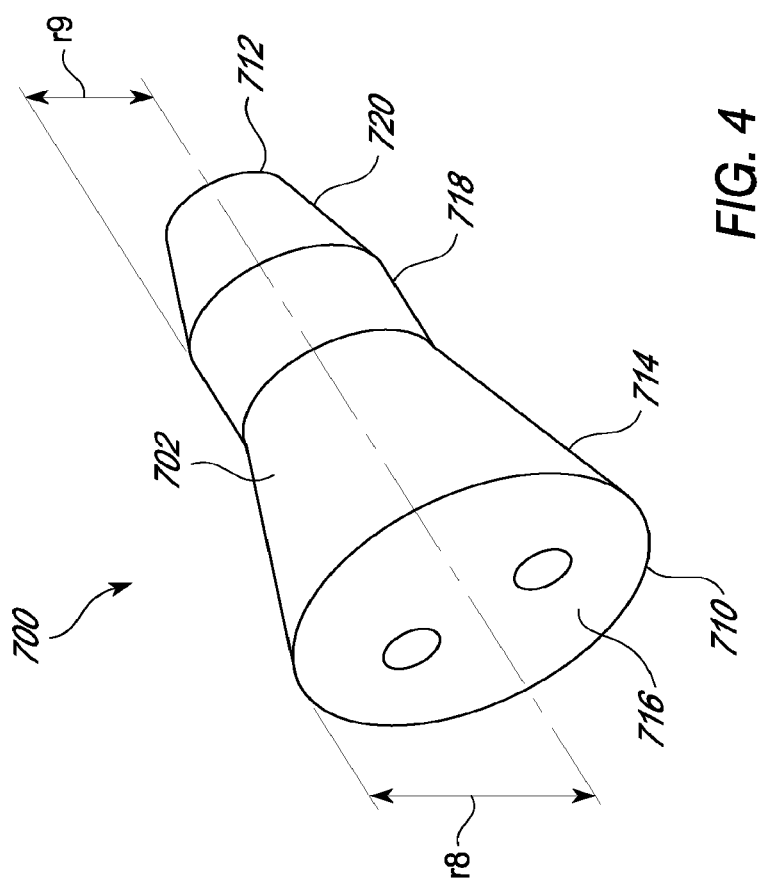
FIG. 4 depicts a perspective view of one embodiment of an expander.

The axial bore 416 can be sized and dimensioned to receive the expander 480. The expander 480 depicted in FIG. 4 is partially disposed within the axial bore 416 of the anchor body 410.

The anchor body 410 depicted in FIG. 1 has plurality of first tines 418 extending from a position proximal to the second end 414 of the anchor body 410 to the first end 412 of the anchor body 410. Each of the first tines 418 is internally defined by the axial bore 416 and radially defined by a plurality of first expansion slots 420. An anchor body can include any desired number of first tines 418 and first expansion slots 420, including 10 or less, 5 or less, 4 or less, or two first tines 418 and first expansion slots 420. The anchor body 410 depicted in FIG. 1 has four first tines 418 and four first expansion slots 420.

The first tines 418 and first expansion slots 420 can be positioned at any desired radial position around the anchor body 410. In some embodiments, the first tines 418 and first expansion slots 420 can be positioned at regular intervals around the anchor body 410. In some embodiments, the first tines 418 and first expansion slots 420 can be irregularly positioned around the anchor body 410. FIG. 1 depicts an embodiment of an anchor body 410 in which the first tines 418 and first expansion slots 420 are equiangularly positioned around the anchor body 410.

Different embodiments of an anchor body 410 can additionally include first tines 418 and first expansion slots 420 of different lengths. In some embodiments, the first tines 418 and first expansion slots 420 of an anchor body 410 can have equal lengths. In some embodiments the first tines 418 and first expansion slots 420 may have different lengths. In some embodiments, the first tines 418 and first expansion slots 420 can be configured to have different lengths in that some of the first tines 418 may extend further from the second end 414 of the anchor body 410 toward the first end 412 of the anchor body 410 than other of the first tines 418. In some embodiments, the first tines 418 and first expansion slots 420 can have different lengths in that some of the first expansion slots 420 can extend further from the first end 412 of the anchor body 410 toward the second end 414 of the anchor body 410 than others of the first expansion slots 420. FIG. 1 depicts an embodiment of an anchor body 410 in which the first tines 418 and first expansion slots 420 have equal lengths.

The anchor body 410 depicted in FIG. 1 has a plurality of second tines 422 extending from a position proximal to the first end 412 of the anchor body 410 toward the second end 414 of the anchor body 410. Each of the second tines 422 is internally defined by the axial bore 416 and radially defined by a plurality of second expansion slots 424. An anchor body can include any desired number of second tines 422 and second expansion slots 424, including 10 or less, 5 or less, 4 or less, or two second tines 422 and second expansion slots 424. The anchor body 410 depicted in FIG. 1 has four second tines 422 and four second expansion slots 424.

The second tines 422 and second expansion slots 424 can be positioned at any desired radial position around the anchor body 410. In some embodiments, the second tines 422 and second expansion slots 424 can be positioned at regular intervals around the anchor body 410. In some embodiments, the second tines 422 and second expansion slots 424 can be irregularly positioned around the anchor body 410. FIG. 1 depicts an embodiment of an anchor body 410 in which the second tines 422 and second expansion slots 424 are equiangularly positioned around the anchor body 410.

Different embodiments of an anchor body 410 can additionally include second tines 422 and second expansion slots 424 of different lengths. In some embodiments, the second tines 422 and second expansion slots 424 of an anchor body 410 can have equal lengths. In some embodiments the second tines 422 and second expansion slots 424 may have different lengths. In some embodiments, the second tines 422 and second expansion slots 424 can be configured to have different lengths in that some of the second tines 422 may extend further from the first end 414 of the anchor body 410 toward the second end 414 of the anchor body 410 than other of the second tines 422. In some embodiments, the second tines 422 and second expansion slots 424 can have different lengths in that some of the second expansion slots 424 can extend further from the second end 414 of the anchor body 410 toward the first end 412 of the anchor body 410 than others of the second expansion slots 424. FIG. 1 depicts an embodiment of an anchor body 410 in which the second tines 422 and second expansion slots 424 have equal lengths.

Some embodiments of an anchor body 410 can have a first set of tines 418 and a second set of tines 422 of equal length. Some embodiments of an anchor body 410 can have a first set of tines 418 and a second set of tines 422 of different lengths. FIG. 1 depicts one embodiment of an anchor body 410 in which the first set of tines 418 is longer than the second set of tines 422.

Some embodiments of an anchor body 410 can have first expansion slots 420 and second expansion slots 424 of equal length. Some embodiments of an anchor body 410 can have first expansion slots 420 and second expansion slots 424 of different lengths. FIG. 1 depicts one embodiment of an anchor body 410 in which the first expansion slots 420 are longer than the second expansion slots 424.

The first tines 418 and first expansion slots 420 and the second tines 422 and second expansion slots 424 allow the expansion of the anchor body 410 when the expander 480 is moved longitudinally in a direction from the first end 412 towards the second end 414 of the anchor body. When the anchor 400 is placed within a hole in a bone, the longitudinal displacement of the expander 480 towards the second end 414 of the anchor body 410 results in the radial expansion of the anchor body 410, and specifically results in the radial expansion of the first tines 418 and first expansion slots 420 located at the first end 412 of the anchor body and of the second tines 422 and second expansion slots 424 located at the second end 414 of the anchor body 410. In some embodiments, the anchor body 410 can be sized and dimensioned relative to the hole in which the anchor 100 is placed, so that the radial expansion of the anchor body resulting from the longitudinal displacement of the expander 480 towards the second end 414 causes the first tines 418 and the second tines 422 to engage with bone surrounding the hole in which the anchor 400 is positioned. In some embodiments, the engagement of the bone by the first tines 418 and the second tines 422 can be facilitated by teeth 428 located on some or all of the first tines 418 and/or the second tines 422. FIG. 1 depicts one embodiment of an anchor body 410 in which teeth 428 are located on all of the first tines 418 and the second tines 422. In some embodiments, the teeth (or ridges) 428 are designed to prevent the anchor 400 from displacing out of the bone. In some embodiments, the teeth 428 are designed to stabilize the anchor 400 in the bone. In some embodiments, the teeth 428 are designed to hold the anchored tissue in proximity to the bone. In some embodiments, the teeth 428 are designed to perform a combination of these and other functions.

In some embodiments, the teeth 428 may penetrate the bone, the teeth 428 may partially penetrate the bone, the teeth 428 may form depressions in the bone, or the teeth 428 may deform to fit to the bone.

In some embodiments, all of the teeth 428 on the anchor body 410 are similarly sized and dimensioned. An anchor body 410 may also have two or more types of teeth 428. Specifically, an anchor body 410 may have a first set of teeth located proximate to the first end 412 of the anchor body 410 on some or all of the first tines 418, and a second set of teeth located proximate to the second end 414 of the anchor body 410 on some or all of the second tines 422.

Figure 2:
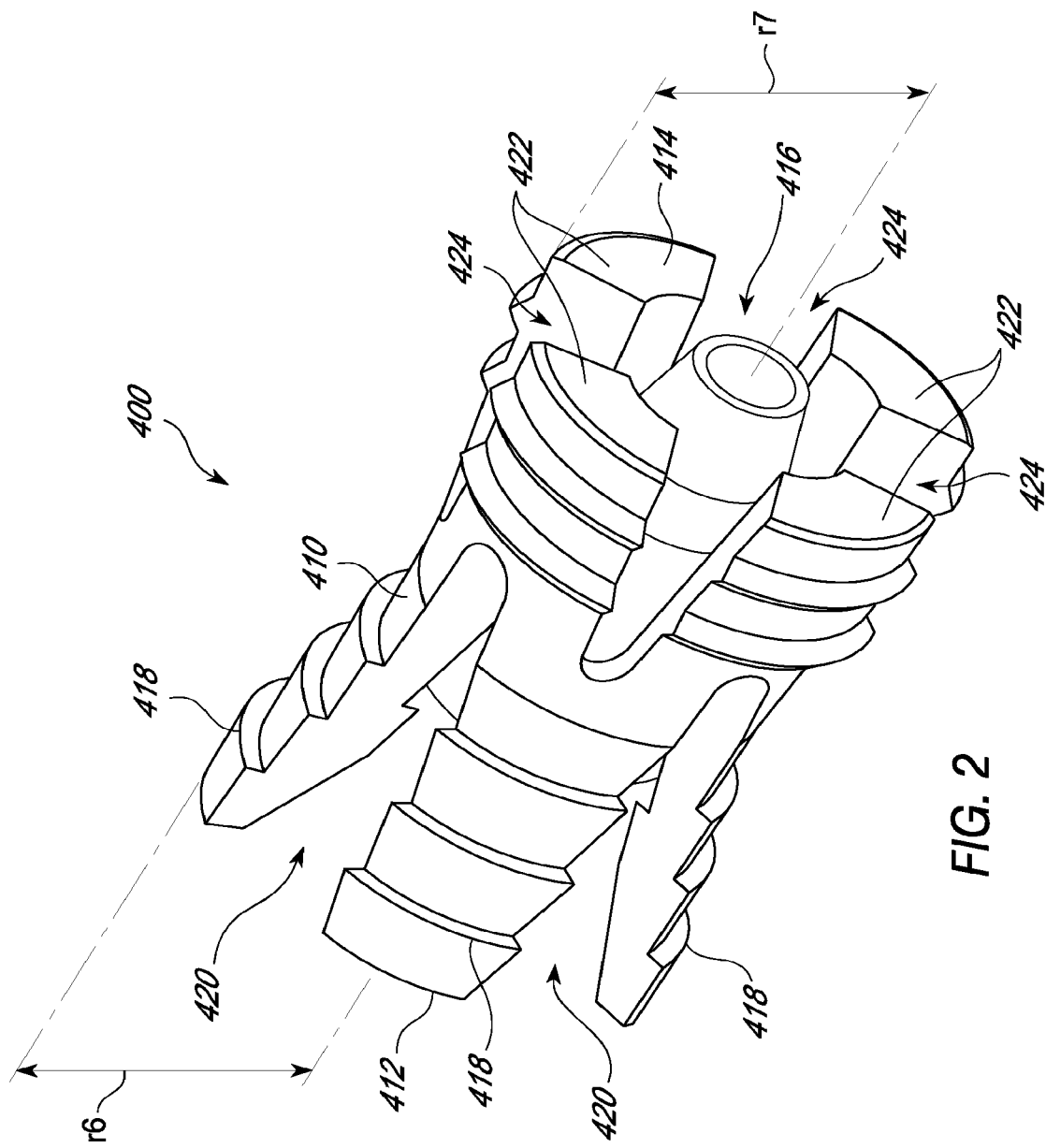
FIG. 2 depicts a perspective view of one embodiment of a bone anchor in a deployed or expanded state.

FIG. 2 depicts a perspective view of one embodiment of the dual expansion anchor 400 comprising an anchor body 410 and an expander 480. The body 410 of the anchor 400 depicted in FIG. 2 has a first end 412, a second end 414, an axial bore 416, first tines 418, first expansion slots 420, second tines 422, second expansion slots 424, and teeth 428. As depicted in FIG. 2, the expander 480 is completely positioned within the axial bore 416 of the anchor body 410. With the expander 480 positioned completely within the axial bore 416 of the anchor body 410, the first end 412 of the anchor body 410 has a new radius r6 and the second end 414 of the anchor body 410 has a new radius r7. The expansion of the anchor body 410 caused by the new positioning of the expander 480 results in radius r6 at the first end 412 of the anchor body 410 being larger than radius r4 at the first end 412 of the anchor body 410 as depicted in FIG. 1, and in radius r7 at the second end 414 of the anchor body 410 being larger than radius r5 at the second end 414 of the anchor body 410 as depicted in FIG. 1. In some embodiments r6 and r7 are the same. In some embodiments r6 and r7 are different. Additionally, while FIGS. 1 and 2 depict an anchor 400 defined respectively by two radii r4, r5 or r6, r7, a person of skill in the art will recognize that a plurality of constant or non-constant radii can define some embodiments of an anchor 400. Thus, an expanded anchor 400 may have uniform or non-uniform radial expansion between a first end 412 and a second end 414.

Figure 3:
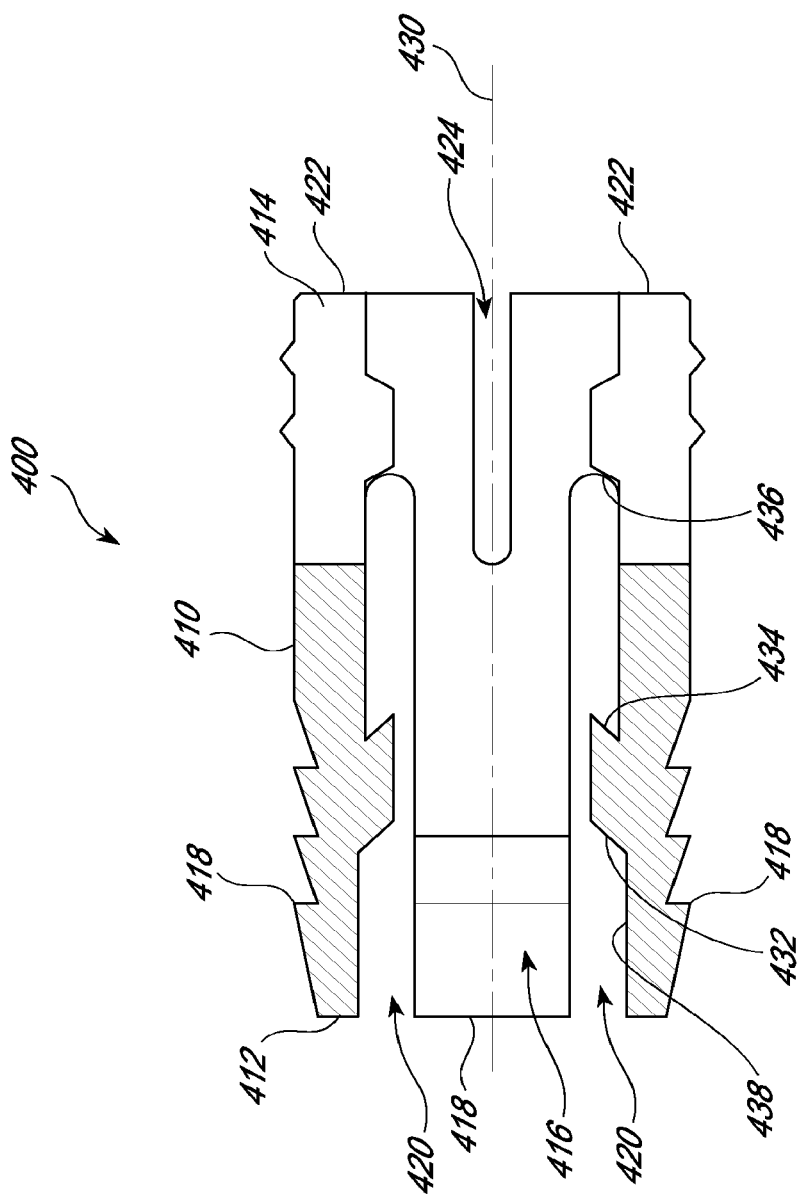
FIG. 3 depicts a cut-away view of one embodiment of a bone anchor in an undeployed or unexpanded state.

FIG. 3 depicts a perspective cut-away view of the same embodiment of the dual expansion anchor 400 comprising an anchor body 410 configured for use with an expander (not shown). The body 410 of the anchor 400 depicted in FIG. 3 has a first end 412, a second end 414, an axial bore 416, first tines 418 and first expansion slots 420, second tines 422 and second expansion slots 424. An axial bore 416 has a longitudinal axis 430 and can comprise a variety of shapes and sizes. In some embodiments, an axial bore may have a single shape and constant diameter throughout the length of the anchor body 410. In some embodiments, and as depicted in FIG. 3, the shape and size of the axial bore 416 may vary along the length of the anchor body 410. A person of skill in the art will recognize that variations in the shape and size of the axial bore 416 can be used in connection with variations in the size and shape of the expander (not shown) to achieve desired expansion of the anchor body 410, to achieve desired placement of the expander (not shown) within the anchor body 410, and to facilitate and/or prevent certain movements of the expander (not shown) within the anchor body 410.

As depicted in FIG. 3, an axial bore 416 can comprise portions that are parallel to the longitudinal axis 430 of the axial bore 416, perpendicular to the longitudinal axis 430 of the axial bore 416, or angled relative to the longitudinal axis 430 of the axial bore 416. The axial bore 416 can comprise a first sloped portion 432. The first sloped portion 432 can be located proximate to the first end 412 of the anchor body 410, or as depicted in FIG. 3, separated from the first end 412 of the anchor body 410 by a parallel portion 438, parallel to the longitudinal axis 430 of the axial bore 416. The first sloped portion 432 can be configured to provide a cam surface for the expander (not shown) to facilitate movement of the expander (not shown) into the axial bore 416 and to thereby facilitate expansion of the radius of the first end 412 of the anchor body 410 from radius r4 to radius r6.

The axial bore 416 can include a first stop 434. As depicted in FIG. 3, a first stop 434 is a wall non-parallel to the longitudinal axis 430 of the anchor body 410. As depicted in FIG. 3, the first stop 434 can be configured to provide an engageable surface to interact with portions of the expander (not shown) and thereby prevent the expander (not shown) from retracting once the expander (not shown) has advanced past a designated point. Advantageously, prevention of the retraction of the expander (not shown) enables the permanent placement of an anchor 400 in bone.

A first stop can be located a desired distance from the first end 412 so as to achieve a desired degree of spreading of the first end 412 of the anchor body 410. In some embodiments, the first stop 434 can be located so that the first end 412 of the anchor body 410 achieves an expanded radius of approximately 40 millimeters, 20 millimeters, 10 millimeters, 5 millimeters, 2 millimeters, 1 millimeter, or any other desired diameter.

The axial bore 416 can comprise a second sloped portion 436. As depicted in FIG. 3, the second sloped portion 436 can be located proximate to the second end 414 of the anchor body 410. The second sloped portion 436 can be configured to provide a cam surface for the expander (not shown) to facilitate movement of the expander (not shown) down the axial bore 416 and to thereby facilitate expansion of the radius of the second end 414 of the anchor body 410 from radius r5 to radius r7. In some embodiments, the second end 414 of the anchor body 410 achieves an expanded radius of approximately 40 millimeters, 20 millimeters, 10 millimeters, 7.2 millimeters, 5 millimeters, 2 millimeters, 1 millimeter, or any other desired diameter.

An anchor can be used with a variety of expanders. FIG. 4 depicts one embodiment of an expander 700 comprising an expansion member 702 having a first end 710 and a second end 712. An expansion member 702 can have one or more features configured to cause expansion of an anchor body when the expander 700 is longitudinally displaced into the anchor body. The expander 700 depicted in FIG. 4 has a spreading head 714 having a radius r8 and located proximate to the first end 710 of the expansion member 702. The spreading head 714 can be manufactured to any desired size and shape. As depicted in FIG. 4, spreading head 714 can comprise a conical frustum having a base 716 located at the first end 710 of the expander. A person of skill in the art will recognize that the shape and size of the head 714 will affect the ultimate degree and shape of expansion of the anchor body, as well as the requisite forces to longitudinally displace the expander 700 within the anchor body.

Figure 7:
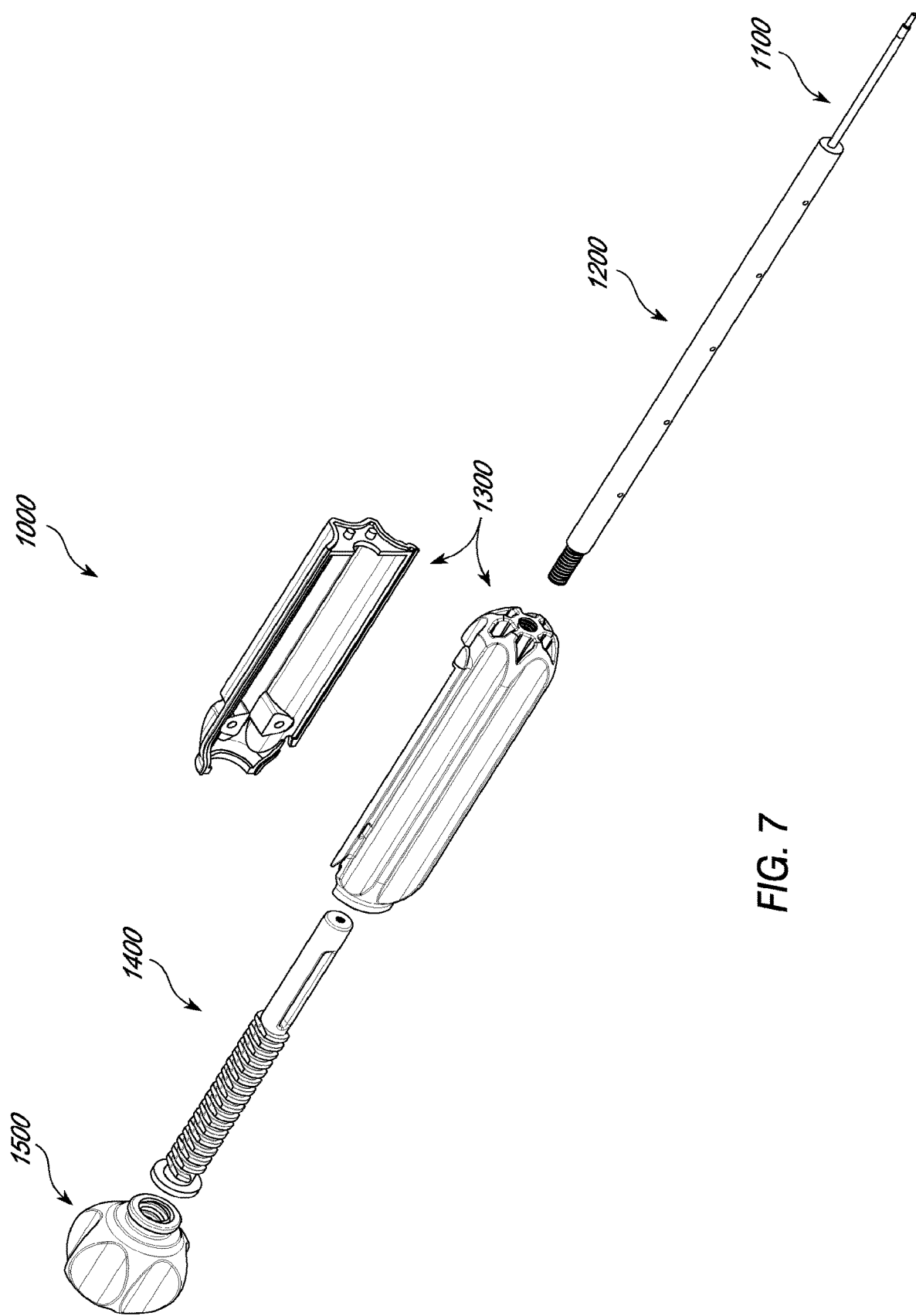
FIG. 7 depicts an exploded perspective view of one embodiment of an inserter tool.

In some embodiments, an expansion member 702 can include a shaft 718 having a diameter r9. As depicted in FIG. 4, shaft 718 can extend longitudinally from the spreading head 714 to the second end 712 of the expansion member 702. Shaft 718 can have a variety of sizes and shapes. The shaft 718 depicted in FIG. 7 is a conical shaft. In some embodiments, the shaft 718 can have a diameter r9 configured to fit within the axial bore of an anchor body without causing expansion of the anchor body. Thus, in some embodiments, expander 700 can be non-expandingly disposed within the axial bore of the anchor body when the shaft 718 is located in the axial bore and features of the expansion member 702 configured for expanding the anchor body are positioned so as to not cause expansion of the anchor body.

In some embodiments, and as depicted in FIG. 4, the shaft 718 can comprise a caming surface 720. In some embodiments, caming surface 720 can, for example, facilitate placement of the expander 700 in an axial bore of an anchor, or facilitate the expansion of the anchor body.

In some embodiments, an expander 700 can include features to facilitate application of forces to the expander 700 to affect deployment of the anchor. In some embodiments, an expander 700 can comprise a threaded hole in the second end 712 configured for threading engagement with a threaded portion of the insertion tool. In some embodiments of an anchor in which the anchor is deployed or expanded by the proximal movement of the expander 700 relative to the anchor, the anchor body can abut with a portion of the insertion tool so as to prevent movement of the anchor body relative to the insertion tool. The expander 700 can be connected to a portion of the insertion tool that is relatively movable as compared to the portion of the insertion tool against which the anchor body abuts. In some embodiments, the abutting interaction of the anchor body and the insertion tool, and the connection of the expander 700 to a relatively movable portion of the insertion tool can allow the longitudinal displacement of the expander from a first, undeployed, unexpanded position proximate to the distal end of the anchor toward the proximate end of the anchor and to a second, deployed, expanded position.

An expander can include features configured for engaging with and capturing material to be secured to the bone, such as, for example, tissue or a suture. These features can be located on a variety of portions of the expansion member 702, including, for example, the head 714, shaft 718, or any other feature configured for expansion.

FIG. 5 depicts one embodiment of a single piece expander 800 comprising and expansion member 802 having a first end 810 and a second end 812. The expansion member 802 further comprises a spreading head 814 having a radius r10 and having a base 816, a first shaft portion 818 having a radius r11, an spreading shoulder 820 having a radius r12, and a second shaft portion 822 having a radius r13. The spreading head 814 depicted in FIG. 8 comprises a conical frustum having a base at the first end 810 of the single piece expander 800. The base 816 of the spreading head 814 depicted in FIG. 5, is radially elevated above the first shaft portion 818, above the spreading shoulder 820, and above the second shaft portion 822, in that the radius r10 of the base 816 of the spreading head 814 is larger than the radius r11 of the first shaft portion 818, larger than the radius r12 of the spreading shoulder 820, and larger than the radius r13 of the second shaft portion 822. The spreading head 814 can comprise a variety of sizes and shapes and a variety of relative sizes according to application requirements for an anchor.

The expansion member 802 depicted in FIG. 5 comprises a spreading shoulder located between the first end 810 and the second end 812 of the single piece expander 800. However, in other embodiments, the spreading shoulder 820 can be located in other positions on the single piece expander 800, including, at the second end 812 of the single piece expander 800. The spreading shoulder 820 depicted in FIG. 5 is radially elevated above the first shaft portion 818 and above the second shaft portion 822 in that the radius r12 of the spreading should 820 is larger than the radius r11 of the first shaft portion 818 and larger than the radius 813 of the second shaft portion 822. The spreading shoulder 822 can comprise a variety of sizes and shapes and a variety of relative sizes according to application requirements for an anchor. In some embodiments, the spreading shoulder 822 can be radially smaller than, radially equal to, or radially larger than the base 816 of the spreading head 814, than the first shaft portion 818, or than the second shaft portion 822. Likewise, the shapes and dimensions of the other features of the single piece expander can be varied to achieve desired results.

Figure 5A:
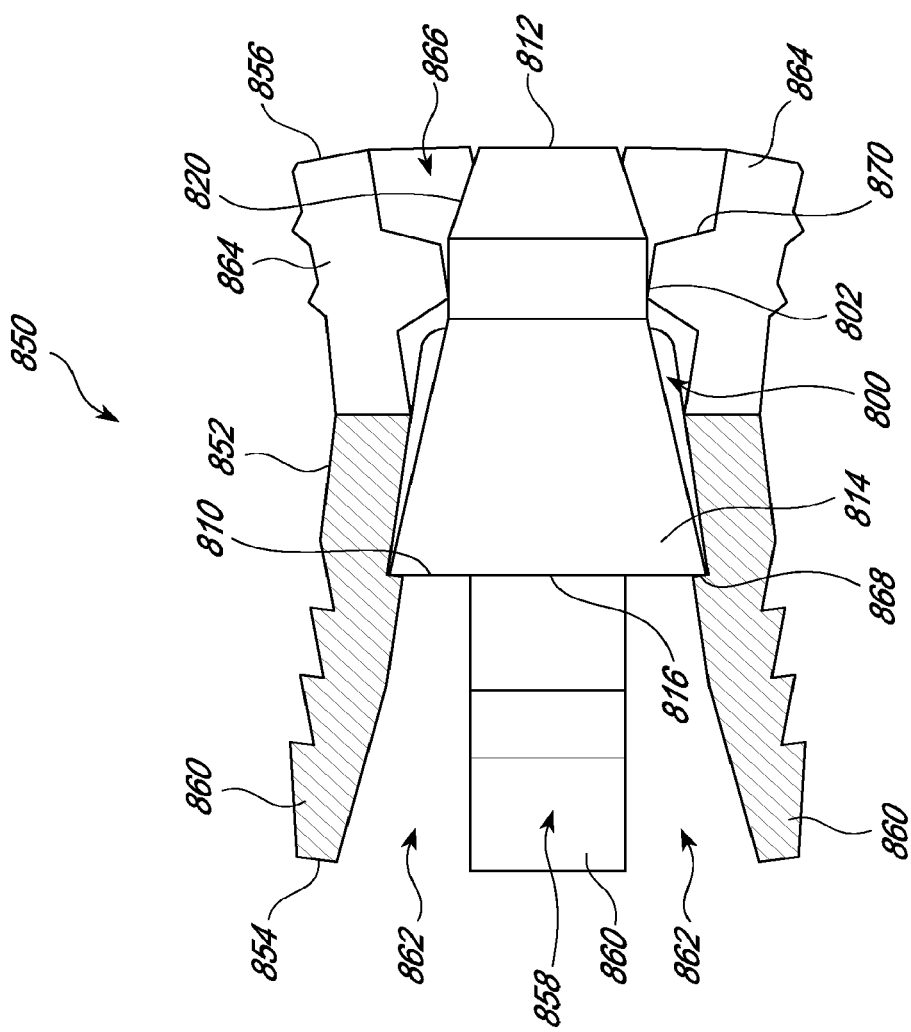
FIG. 5A depicts a cut-away view of one embodiment of a single piece expander deploying a tined dual expansion anchor.

FIG. 5A depicts a perspective cut-away view of an anchor 850 comprising an anchor body 852 and an expander 800 in an expanded or deployed configuration.

The expander depicted in FIG. 5A comprises an expansion member 802 having a first end 810 and a second end 812. The expansion member 802 further comprises a spreading head 814 having a base 816 located at the first end 810. The expansion member additionally comprises a caming surface 820 located proximate to the second end 812 of the expansion member 802 and between the first end 810 of the expansion member 802 and the second end 812 of the expansion member 802.

The anchor body 852 depicted in FIG. 5A comprises a first end 854, a second end 856, an axial bore 858, first tines 860 and first expansion slots 862, second tines 864 and second expansion slots (not shown). The axial bore 858 of the anchor body 852 depicted in FIG. 8A also has a first stop 868 and a earning abutment 870.

As depicted in FIG. 5A, the expander 800 is wholly positioned within the axial bore 858 of the anchor body 850. Specifically, the expander 800 is positioned within the axial bore 858 of the anchor body 850 such that the first stop 868 prevents movement of the expander 800 towards the first end 854 of the anchor body 850 by abuttingly engaging with the base 816 of the spreading head 814 of the expander 800.

As depicted in FIG. 5A, the spreading head 814 and other portions of the expander 800 expandingly engage with portions of the axial bore to deploy or expand the anchor body 850.

Figure 6:
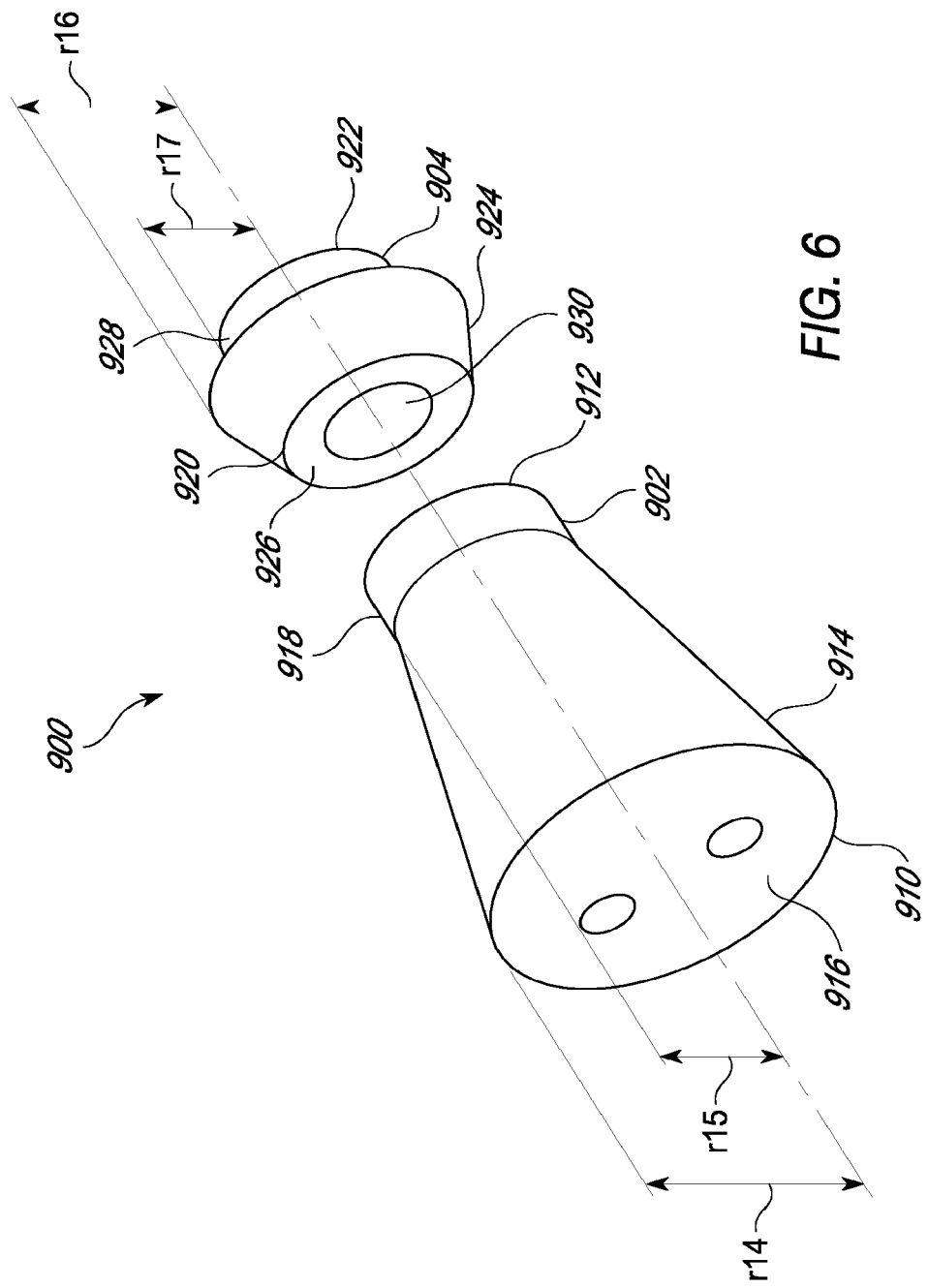
FIG. 6 depicts a perspective view of one embodiment of a two piece expander.

FIG. 6 depicts one embodiment of a two piece expander 900 comprising a first expansion member 902 and a second expansion member 904. In some embodiments, a two piece expander 900 can include features to facilitate application of forces to the expander 900 to affect deployment of the anchor. In some embodiments of an anchor in which the anchor is deployed, or expanded, by the movement of the expander 900 relative to the anchor, the anchor body can abut with a portion of the insertion tool so as to prevent movement of the anchor body relative to the insertion tool. The pieces of the expander 900 can be connected to one or multiple portions of the insertion tool that are relatively movable as compared to the portion of the insertion tool against which the anchor body abuts. In some embodiments, the abutting interaction of the anchor body and the insertion tool, and the connection to the pieces of the expander 900 allow the relatively movable portion of the insertion tool to longitudinally displace the expander pieces from a first, undeployed, unexpanded position to a second, deployed, expanded position.

The first expansion member has a first end 910 and a second end 912. The first expansion member 902 has a first spreading head 914 having a base 916 defined by a radius r14, and a first shaft portion 918 defined by a radius r15. The first spreading head 914 depicted in FIG. 9 comprises a conical frustum having a base 916 at the first end 910 of the first expansion member 902 of the double piece expander 900. The base 916 of the first spreading head 914 depicted in FIG. 6, is radially elevated above the first shaft portion 918 in that the radius r14 of the base 916 of the first spreading head 914 is larger than the radius r15 of the first shaft portion 918. The first spreading head 914 can comprise a variety of sizes and shapes and a variety of relative sizes according to application requirements for an anchor.

The second expansion member 904 has a first end 920 and a second end 922. The second expansion member 904 has a second spreading head 924 having a base 926 defined by a radius r16, and a second shaft portion 928 defined by a radius r17. The second spreading head 924 depicted in FIG. 6 comprises a conical frustum having a base 926 at the first end 920 of the second expansion member 904 of the double piece expander 900. The base 926 of the second spreading head 924 depicted in FIG. 6, is radially elevated above the second shaft portion 928 in that the radius r16 of the base 926 of the second spreading head 924 is larger than the radius r17 of the second shaft portion 928. The second spreading head 924 can comprise a variety of sizes and shapes and a variety of relative sizes according to application requirements for an anchor. The first and second spreading heads 914, 924 can comprise a variety of sizes and shapes and a variety of relative sizes according to application requirements for an anchor. In some embodiments, the base 916 of the first spreading head 914 can be radially smaller than, radially equal to, or radially larger than the base 926 of the second spreading head 924. Similarly, the relative sizes of the first shaft portion 918 and the second shaft portion 928 can vary with respect to each other and with respect to the first and second spreading heads 914, 924.

In some embodiments of a double piece expander 900, the second expansion member can comprise a thru-hole 930. The thru-hole can be sized and shaped to allow a portion of the insertion tool configured for attachment to the first expansion member 902 to pass through the second expansion member 904.

In some additional embodiments, the second end 922 of the second expansion member 904 can be configured for abutting contact with a portion of an insertion tool. In some embodiments, the portion of the insertion tool can be configured to allow movement of the second expansion member 904 relative to the anchor body.

Figure 6A:
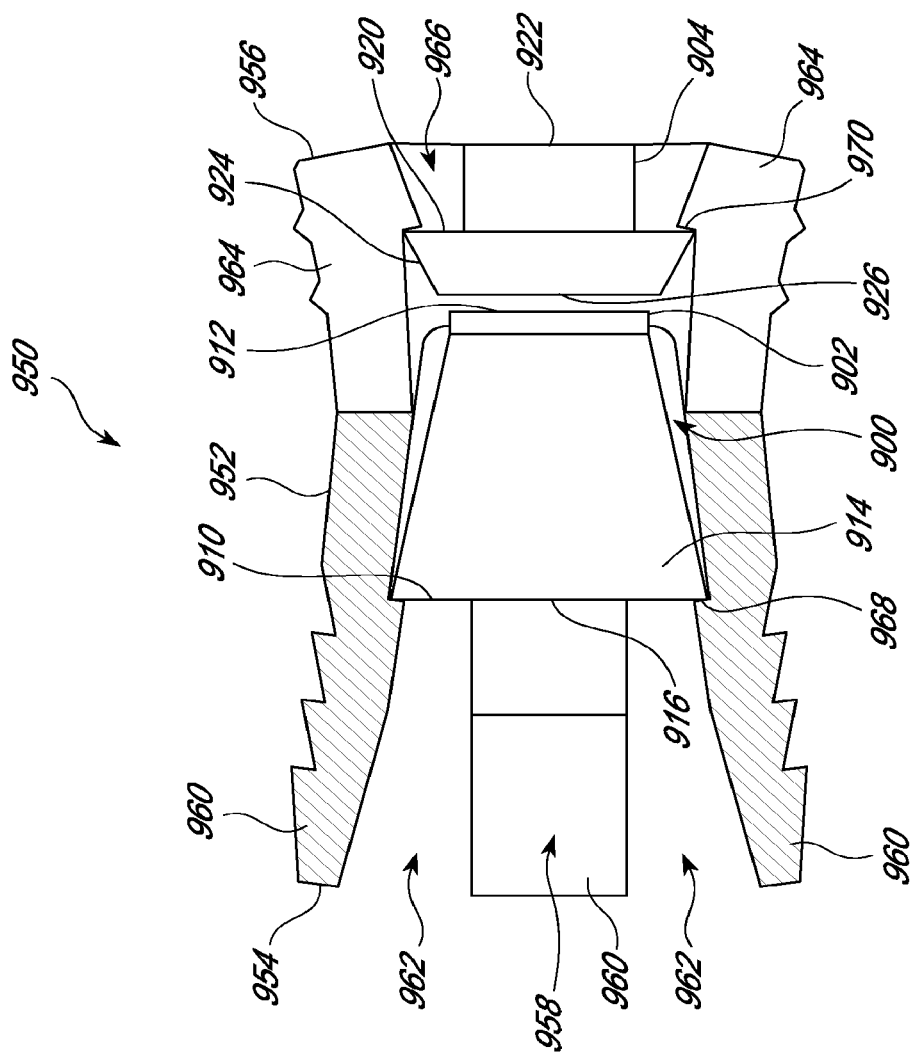
FIG. 6A depicts a cut-away view of one embodiment of a two piece expander deploying a bone anchor.

FIG. 6A depicts a perspective cut-away view of an anchor 950 in an expanded or deployed configuration comprising an anchor body 952 and a double piece expander 900.

The double piece expander 900 depicted in FIG. 6A comprises a first expansion member 902 and a second expansion member 904. The first expansion member 902 has a first end 910 and a second end 912 and comprises a first spreading head 914 having a base 916 located at the first end 910. The second expansion member 904 has a first end 920 and a second end 922 and comprises a second spreading head 924 having a base 926 located at the first end 920.

The anchor body 952 depicted in FIG. 6A comprises a first end 954, a second end 956, an axial bore 958, first tines 960 and first expansion slots 962, second tines 964 and second expansion slots (not shown). The axial bore 958 of the anchor body 952 depicted in FIG. 6A also has a first stop 968 and a second stop 970.

As depicted in FIG. 6A, the expander 900 is wholly positioned within the axial bore 958 of the anchor body 950. Specifically, the expander 900 is positioned within the axial bore 958 of the anchor body 950 such that the first stop 968 prevents movement of first expansion member 902 towards the first end 954 of the anchor body 950 by abuttingly engaging with the base 916 of the first spreading head 914 of the first expansion member 902. The second expansion member 904 of the expander 900 is positioned within the axial bore 958 of the anchor body 950 such that the second stop 970 prevents movement of second expansion member 904 towards the second end 956 of the anchor body 950 by abuttingly engaging with the second spreading head 924 of the second expansion member 904. As additionally depicted in FIG. 6A, the first expansion member 902 is not in contact with second expansion member 904. However, a person of skill in the art will recognize that in some embodiments, a first expansion member 902 may be in contact with a second expansion member 904.

As depicted in FIG. 6A, the first spreading head 914 and the second spreading head 924 expandingly engage with portions of the axial bore to deploy or expand the first tines 960 and first expansion slots 962 located at the first end 954 of the anchor body 950 and the second tines 964 and second expansion slots 966 located at the second end 956 of the anchor body 950 respectively.

The above described dual expansion anchor can be made from a variety of materials, including, natural, or manmade materials. The dual expansion anchor can be made of metal, plastic, polymer, composite, or other materials. In some embodiments, the anchor is made of a biocompatible polymer, plastic, or metal. Other embodiments include a tissue capture anchor entirely or in part of a non-metallic substance that is biocompatible. Biocompatible materials such as poly ether ketone (PEK), polyether ether ketone (PEEK), polyetherimide (ULTEM), ultrahigh molecular weight polyethylene (UHMPE), polyphenylene, or some other engineering polymer materials known to those of skill in the art may be used. A non-metallic anchor system may provide certain advantages such as, for example, eliminating MRI artifacts.

Tissue Capture

Some embodiments include using an anchor described above to capture and secure soft tissue, such as a tendon or ligament, prior to insertion of the anchor into bone. In some embodiments, soft tissue can be secured to the anchor using a loop of suture that passes around soft tissue or a soft tissue bundle. In some embodiments, manipulation of the suture to achieve the secured configuration can be accomplished using a suture grabber that is associated with the anchor. In some embodiments, the suture grabber extends from a distal end of the anchor. In some embodiments, the suture grabber is retractable into the anchor so as to pull a suture limb into the anchor. Suitable suture grabbers can include, but are not limited to, a wire loop, a wire hook, a pincher mechanism, or any other suitable structure. In some embodiments, the suture grabber is formed from a nitinol wire. In any of the embodiments utilizing a particular suture grabber as described herein (e.g., a wire loop), it is to be understood that any other suitable suture grabber may be utilized.

Figure 17A:
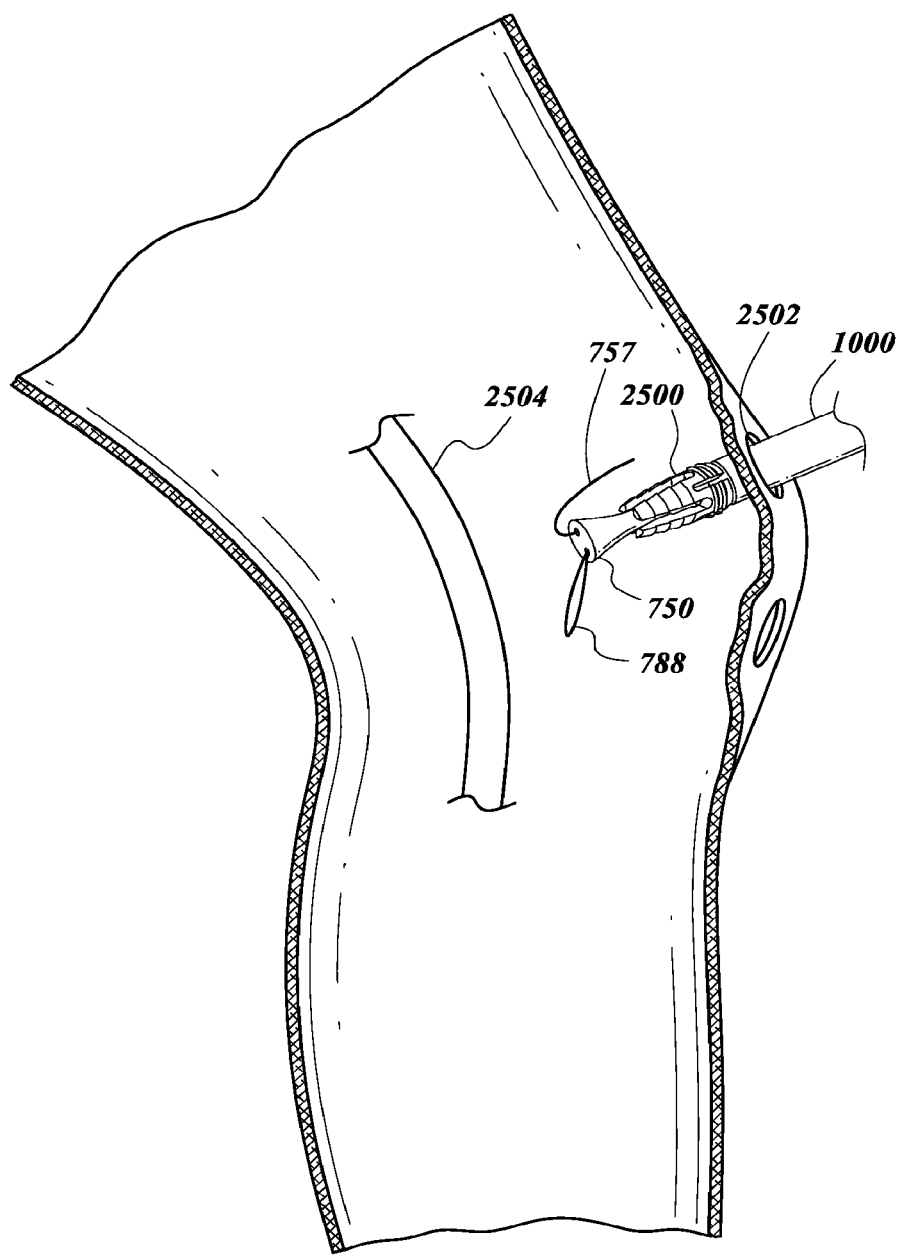
FIGS. 17A to 17E depict a method of using one embodiment of an anchor to secure soft tissue to a bone anchor.
Figure 17B:
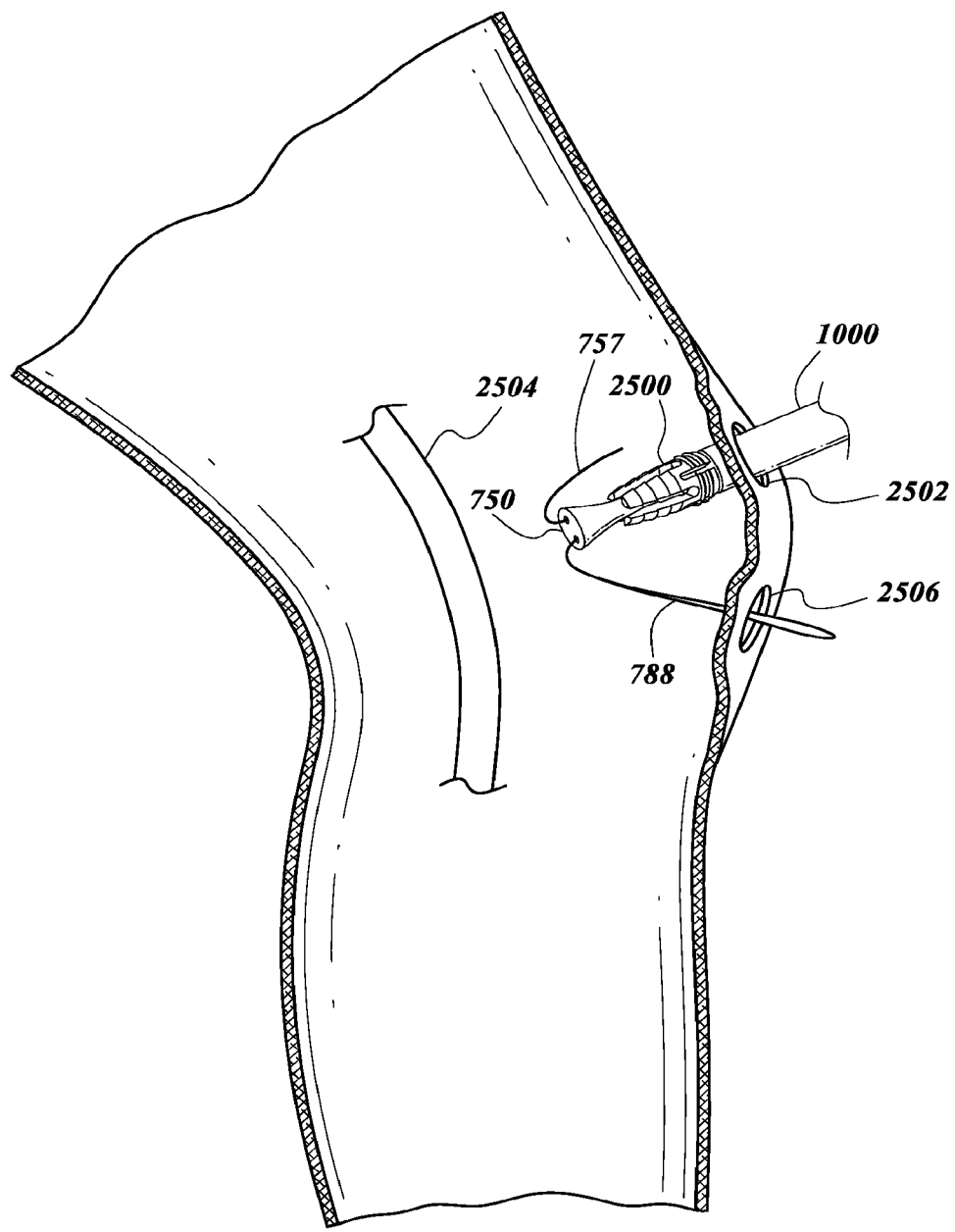

FIGS. 17A through 19E depict embodiments of methods of securing soft tissue, such as, for example, a tendon or ligament, to an anchor 2500 which can be connected to an inserter tool 1000. The anchor 2500 can comprise any of the anchors discussed above, or any other desired anchor. As depicted in FIG. 17A, the anchor 2500 comprises an expander 750 including a suture 757 and a wire loop 788. The suture 757 extends from the anchor through a first hole on the distal end of the anchor expander 750. The wire loop 788 extends from the anchor through a second hole on the distal end of the anchor expander 750. The suture may extend proximally through the interior of the anchor 2500 and the interior of the inserter tool 1000 to a position where it can be held and manipulated by a surgeon. Similarly, the ends of the wire loop 788 may extend proximally through the interior of the anchor 2500 and the interior of the inserter tool 1000 to a position where they can be held and manipulated by a surgeon. As depicted in FIG. 17A, the anchor 2500 can be inserted through a first arthroscopic port 2502 to a position proximate to, for example, a tendon 2504. After the anchor 2500 has been positioned proximate to a tendon 2504, the process proceeds to FIG. 17B and the wire loop 788 can be pulled through a second arthroscopic port 2506. In some embodiments, a tool can be reached through the first arthroscopic port 2502 or the second arthroscopic port 2506 and can be used to grasp the wire loop 788 and to pull the wire loop through the second arthroscopic port 2506.

Figure 17C:
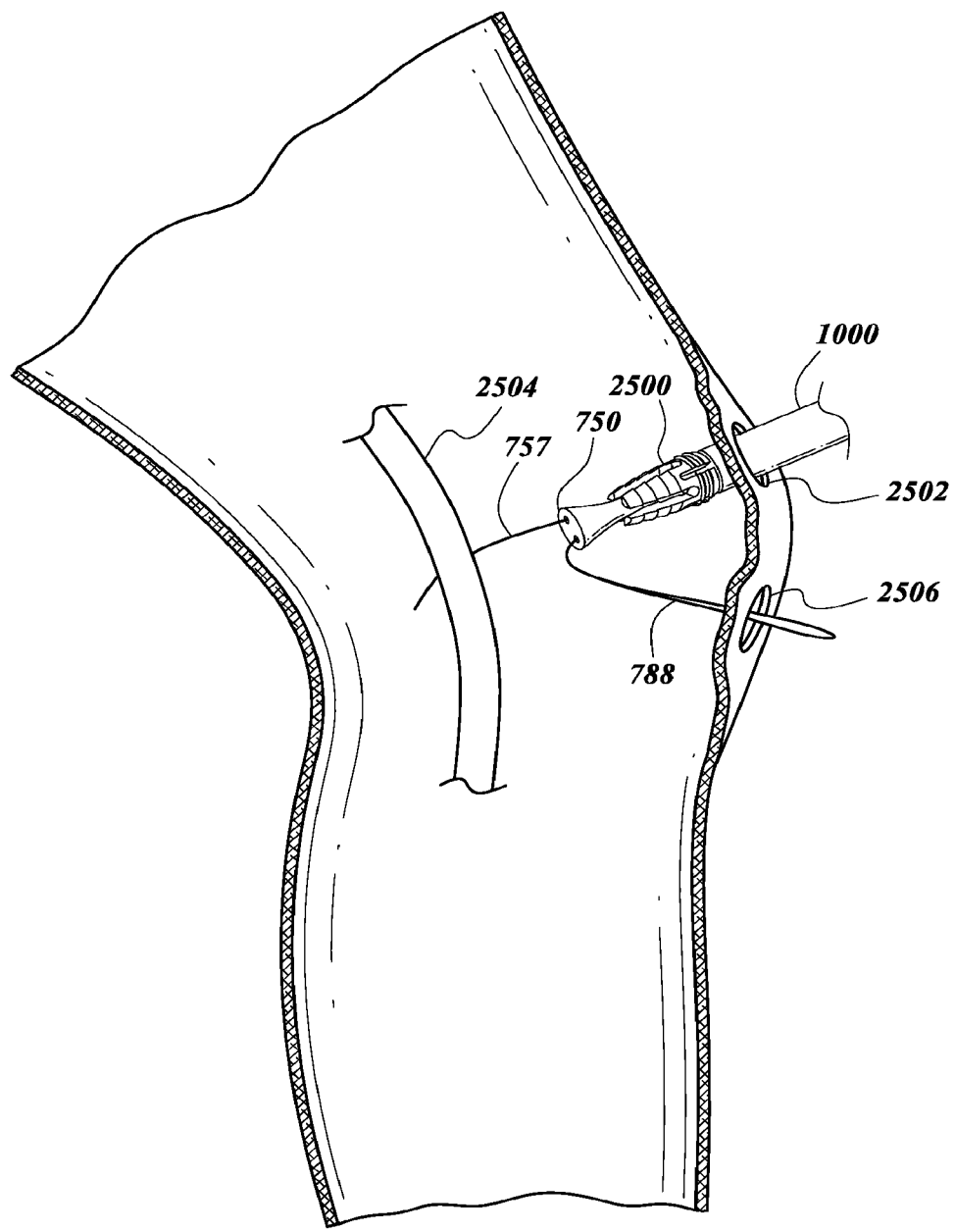
Figure 17D:
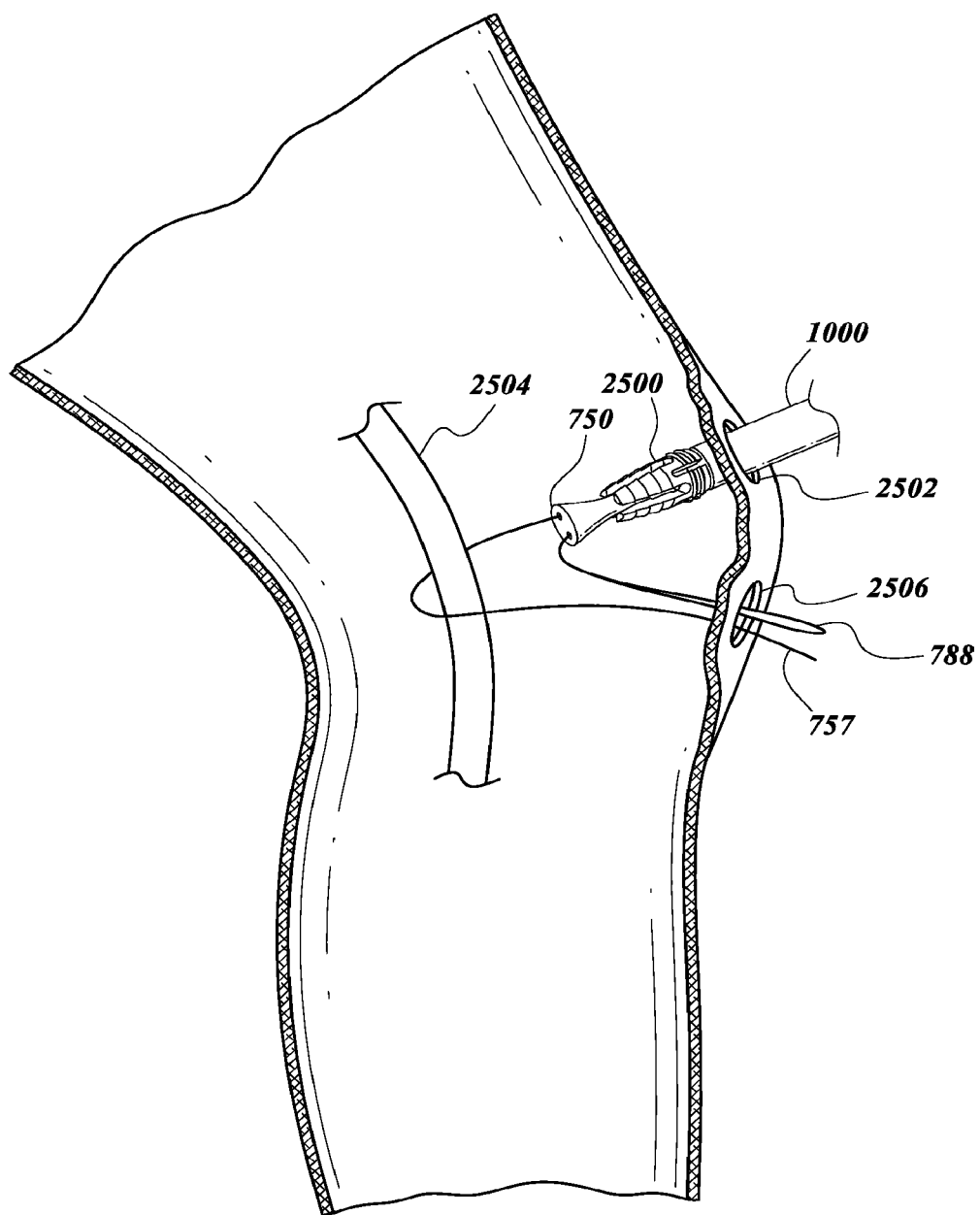
Figure 17E:
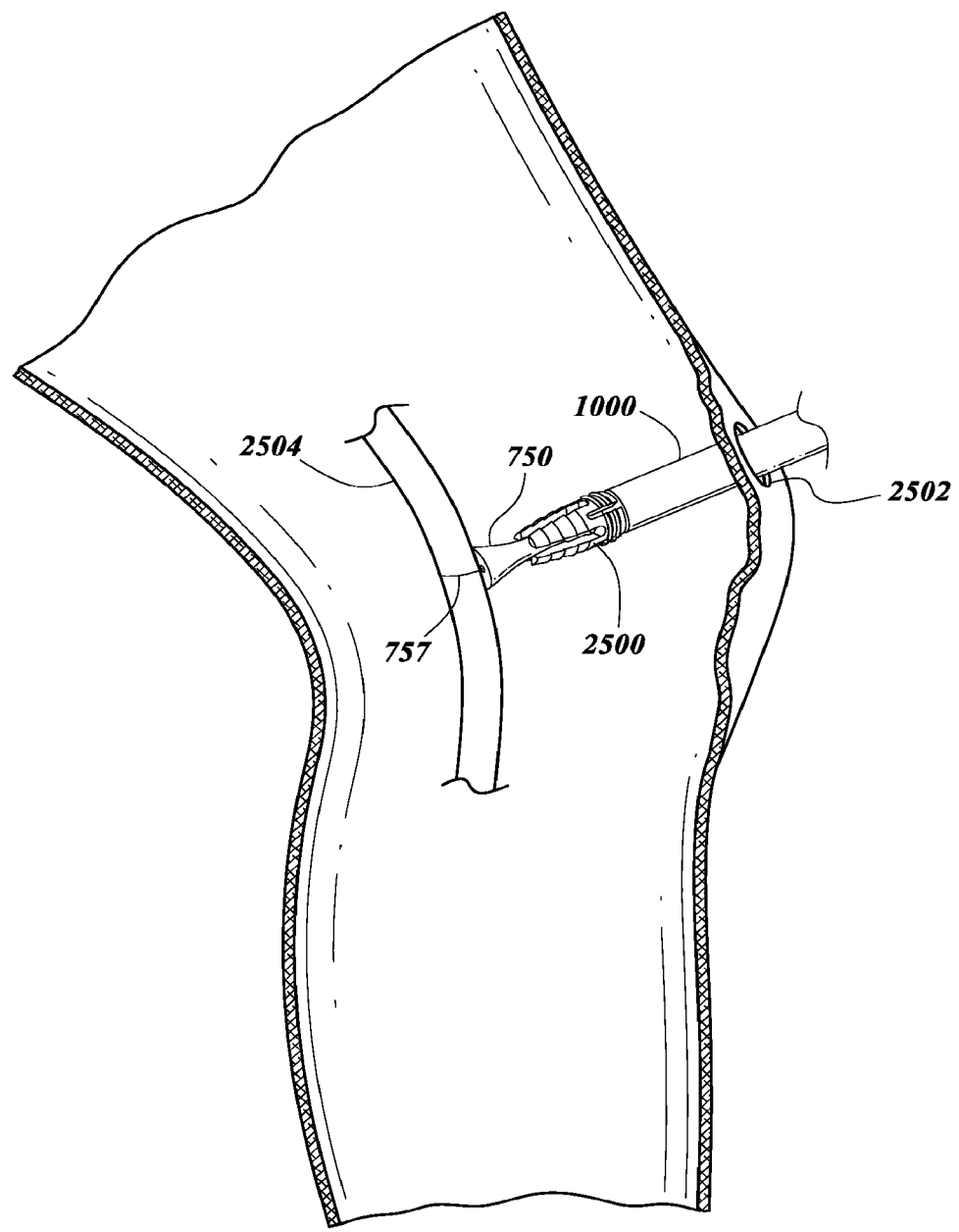

After the wire loop 788 is pulled through a second arthroscopic port 2506, the process proceeds to FIG. 17C, in which the suture 757 can be passed under the, for example, tendon 2504. In some embodiments, a tool can be reached through the first arthroscopic port 2502 or the second arthroscopic port 2506 and can be used to grasp the suture 757 to pass the suture 757 under the tendon 2504. After the suture 757 is passed under the tendon 2504, the process proceeds to FIG. 17D, and the suture 757 is pulled through the second arthroscopic port 2506. As discussed above, a tool can access the suture 757 via one of the arthroscopic ports 2502, 2506 and can pull the suture 757 out of the second arthroscopic port. After the suture 757 is pulled through the second arthroscopic port 2506, the suture 757 can be passed through or tied to the wire loop 788.

Next, the wire loop 788 may be retracted (e.g., by pulling on the ends of the wire that extend through the anchor inserter 1000) down through the arthroscopic port 2506, through the interior of the anchor 2500 and interior of the inserter 1000, and out of the patient's body in the vicinity of the inserter 1000. Advantageously, the retraction of the wire loop 788 through these features can likewise retract the limb of the suture 757 that extends through port 2506 through these features. After the wire loop 788 is retracted, pulling the suture 757 with it, the process moves to FIG. 17E and the tendon 2504 is secured to the anchor 2500 by the suture 757 which forms a loop around the tendon 2504 with its two suture limbs extending through the interior of the anchor 2500 and the interior of the inserter 1000. In some embodiments, the tendon may be temporarily and adjustably secured to the anchor by creating tension on the two suture limbs. This tension may be manually created by a surgeon pulling on the suture limbs or the suture limbs may be secured to a portion of the inserter 1000, such as suture cleats located on a handle of the inserter 1000.

Figure 18A:
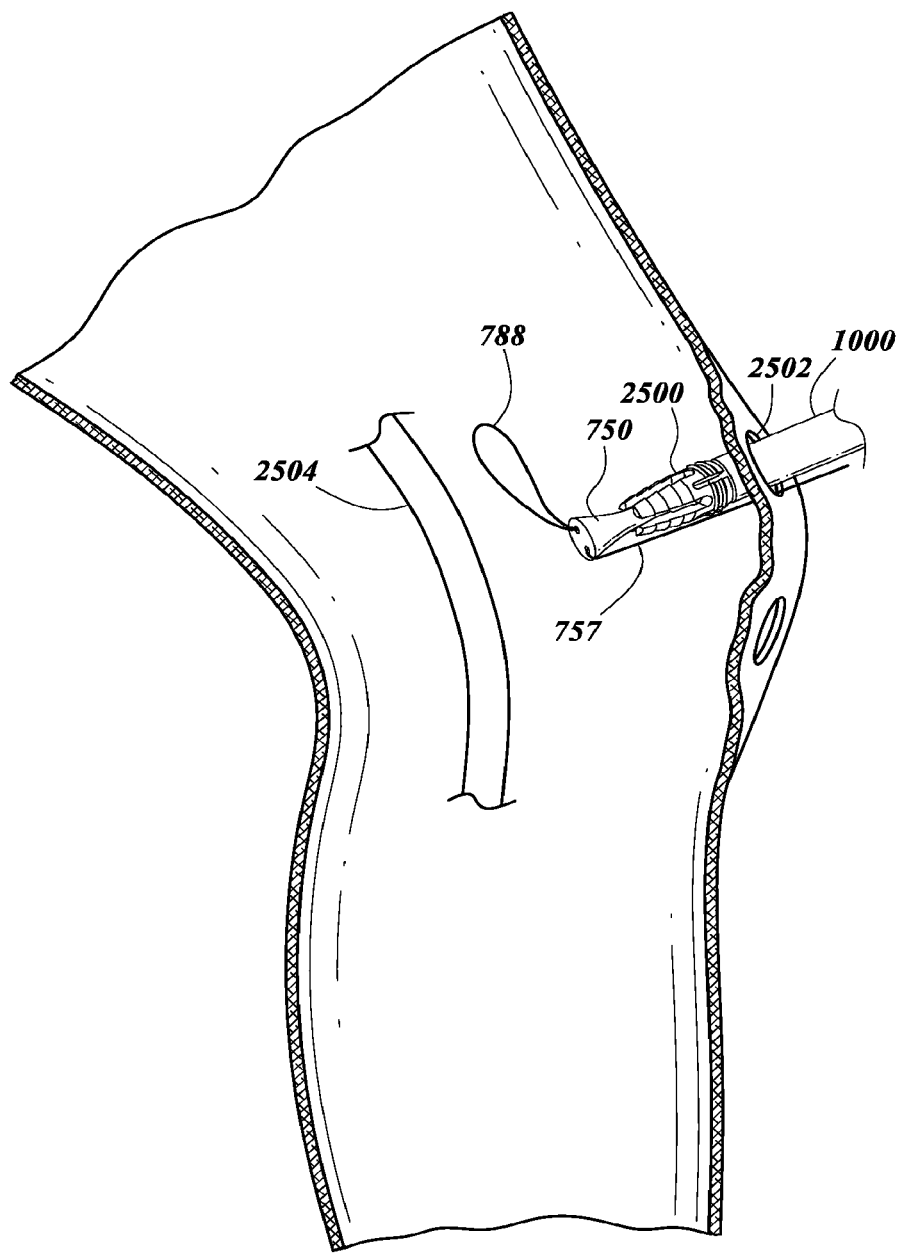
FIGS. 18A to 18E depict a method of using one embodiment of an anchor to secure soft tissue to a bone anchor.

FIGS. 18A through 18E depict another method of securing soft tissue to an anchor 2500. As depicted in FIG. 18A, the anchor 2500 comprises a wire loop 788 and a suture 757. The suture 757 extends from the anchor through a first hole on the distal end of the anchor expander 750. The wire loop 788 extends from the anchor through a second hole on the distal end of the anchor expander 750. The suture may extend proximally through the interior of the anchor 2500 and the interior of the inserter tool 1000 to a position where it can be held and manipulated by a surgeon. Similarly, the ends of the wire loop 788 may extend proximally through the interior of the anchor 2500 and the interior of the inserter tool 1000 to a position where they can be held and manipulated by a surgeon. The suture 757 is inserted through the first arthroscopic port 2502 to a position proximate to, for example, the tendon 2504. As further depicted in FIG. 18A, the suture 757 can, in some embodiments, extend through the expander 750 of the anchor 2500 and out the first arthroscopic port 2502. In some embodiments, the two limbs of the suture 757 can be affixed, for example, to the cleats on the inserter 1000.

Figure 18B:
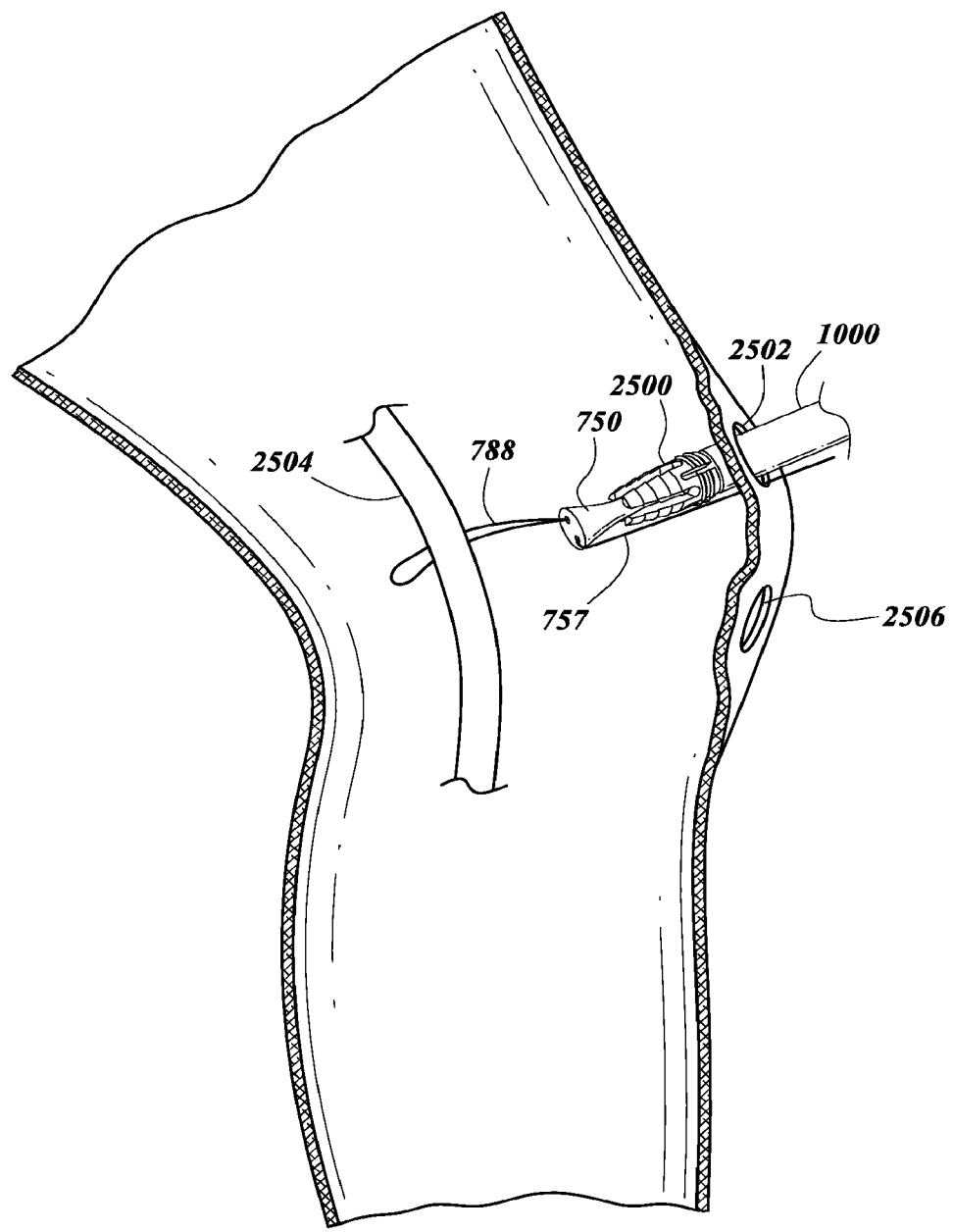
Figure 18C:
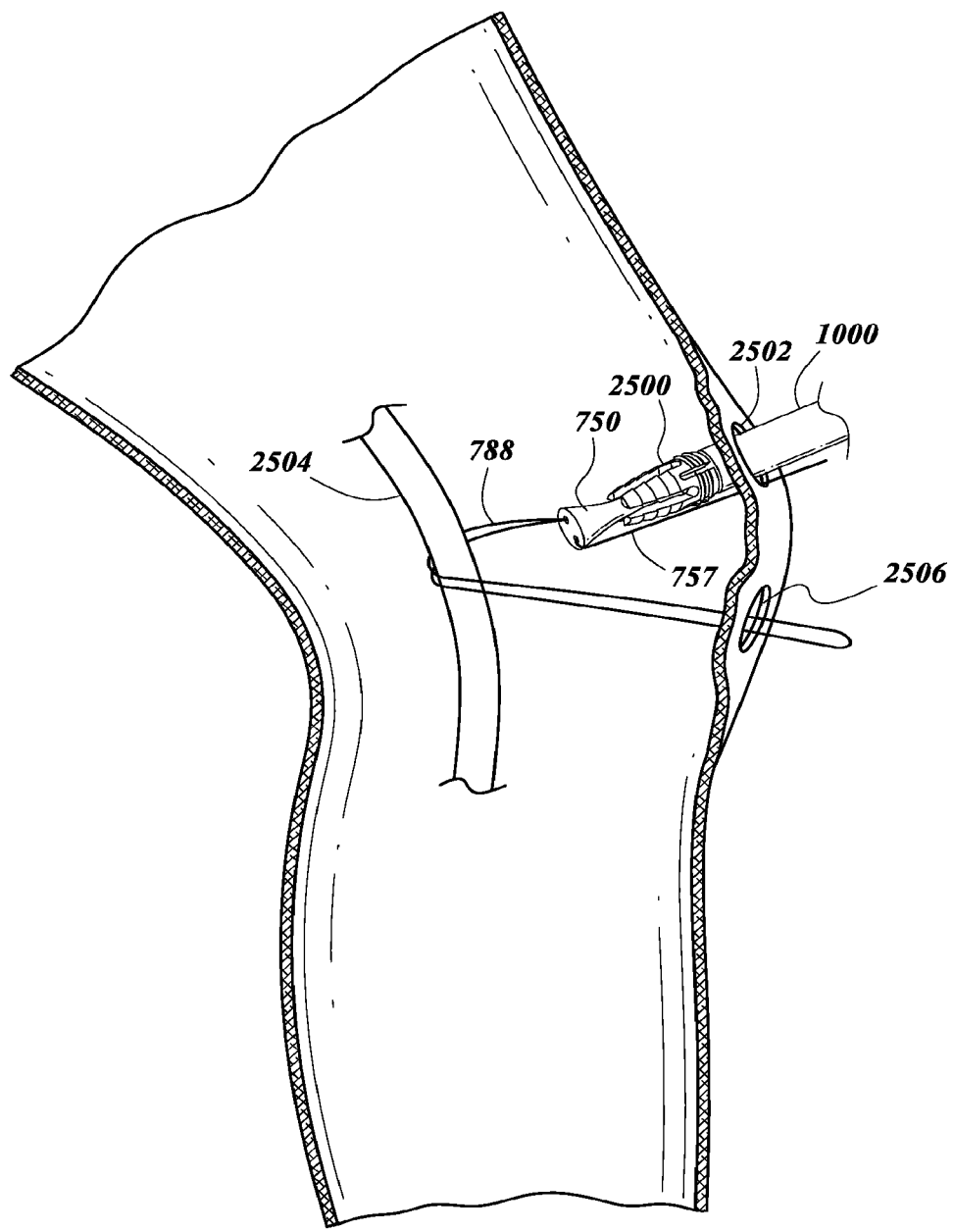
Figure 18D:
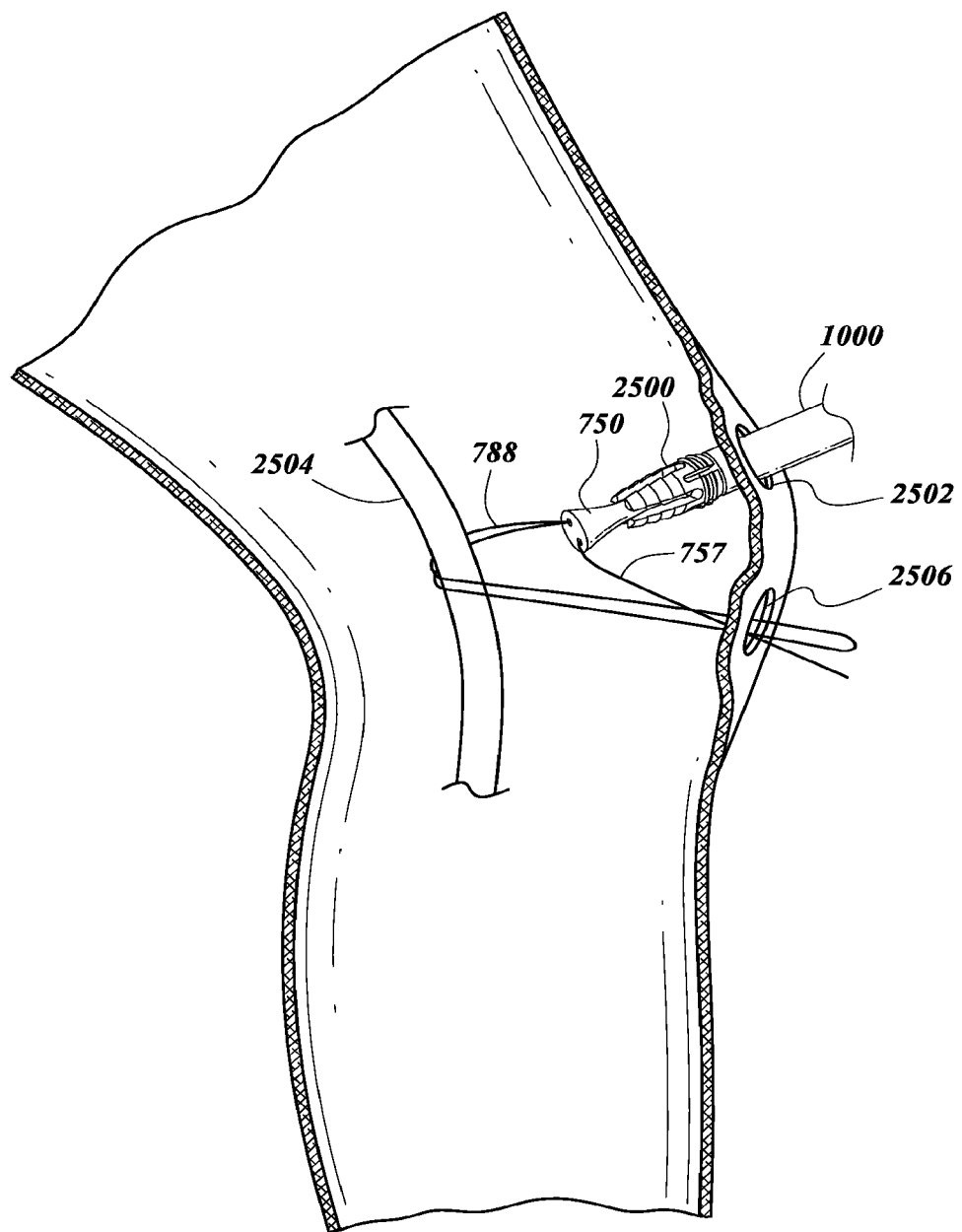
Figure 18E:
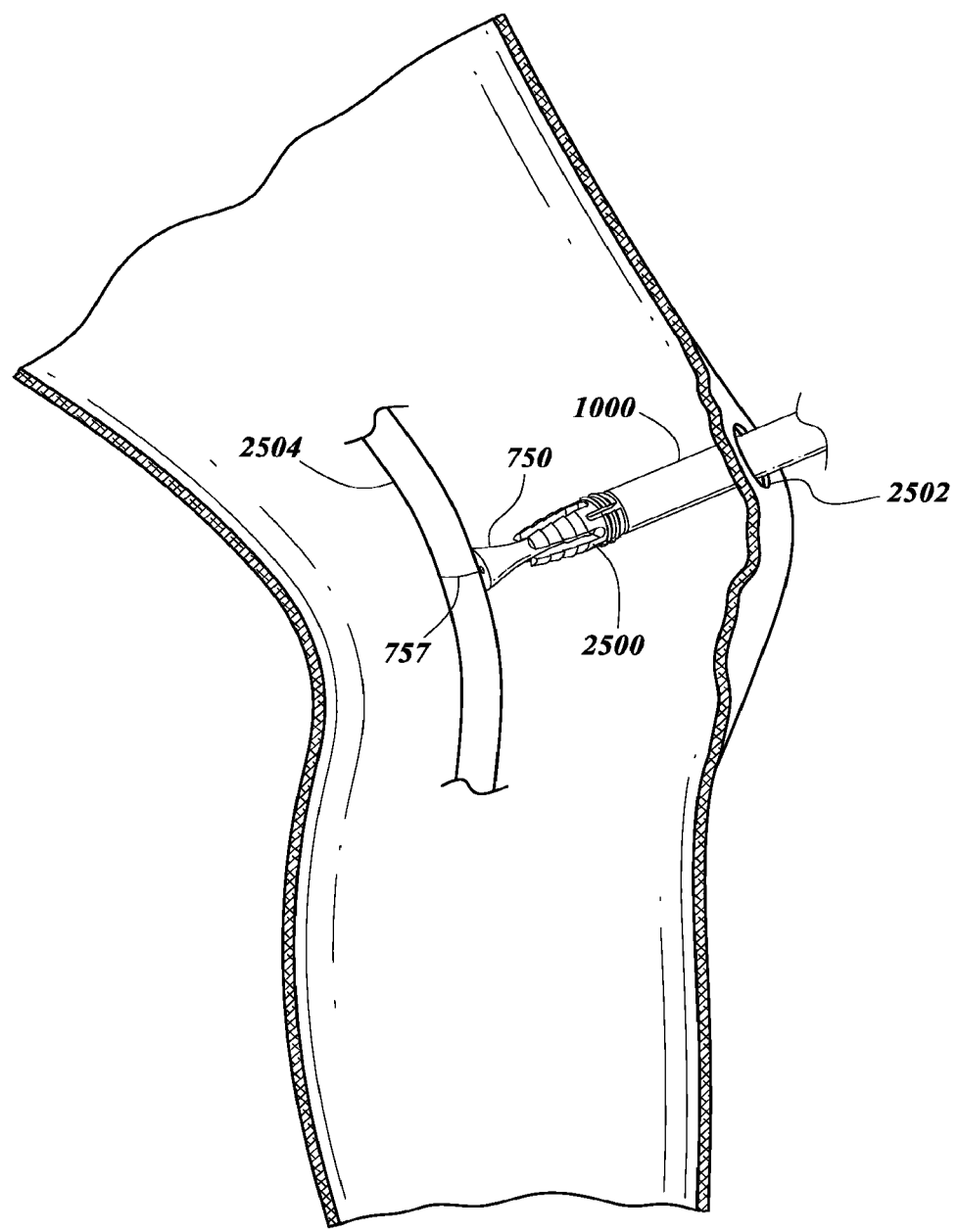

After the anchor 2500 is positioned proximate to the tendon 2504, the process proceeds to FIG. 18B and the wire loop 788 is passed under, for example, the tendon 2504. After the wire loop 788 is passed under the tendon 2504, the process proceeds to FIG. 18C, and the wire loop 788 is pulled through the second arthroscopic port 2506. After the wire loop 788 is pulled through the second arthroscopic port 2506, the process proceeds to FIG. 18D, in which the suture 757 can be released from a cleat on the inserter, and the suture can be pulled through the second arthroscopic port 2506 and passed through the wire loop 788. Next, the wire loop 788 may be retracted (e.g., by pulling on the ends of the wire that extend through the anchor inserter 1000) down through the arthroscopic port 2506, through the interior of the anchor 2500 and interior of the inserter 1000, and out of the patient's body in the vicinity of the inserter 1000. Advantageously, the retraction of the wire loop 788 through these features can likewise retract the limb of the suture 757 that extends through the port 2506 through these features. After the wire loop 788 is retracted, pulling the suture 757 with it, the process moves to FIG. 18E and the tendon 2504 is secured to the anchor 2500 by the suture 757 which forms a loop around the tendon 2504 with its two suture limbs extending through the interior of the anchor 2500 and the interior of the inserter 1000. In some embodiments, the tendon may be temporarily and adjustably secured to the anchor by creating tension on the two suture limbs. This tension may be manually created by a surgeon pulling on the suture limbs or the suture limbs may be secured to a portion of the inserter 1000, such as suture cleats located on a handle of the inserter 1000.

Figure 19A:
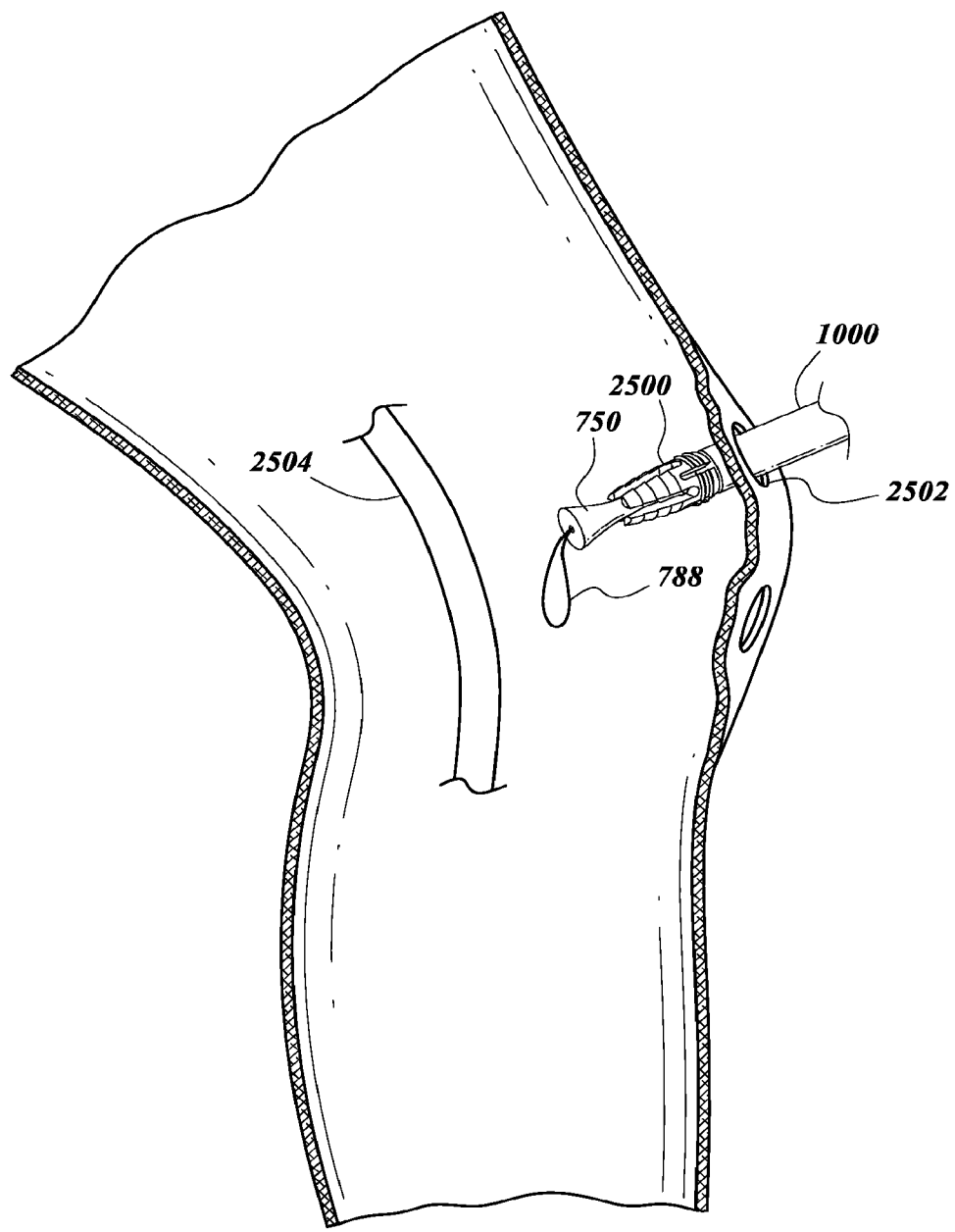
FIGS. 19A to 19E depict a method of using one embodiment of an anchor to secure soft tissue to a bone anchor.
Figure 19B:
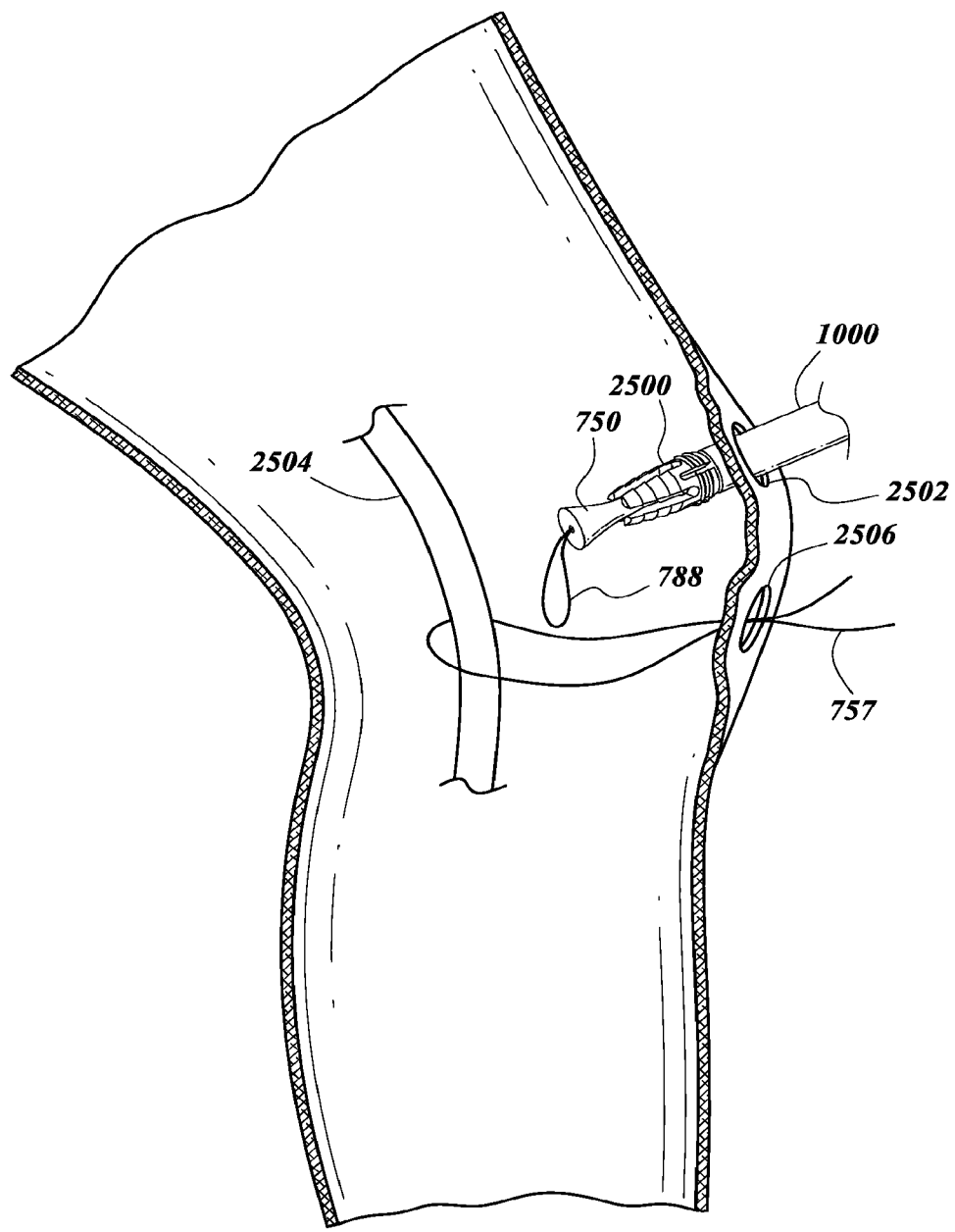
Figure 19C:
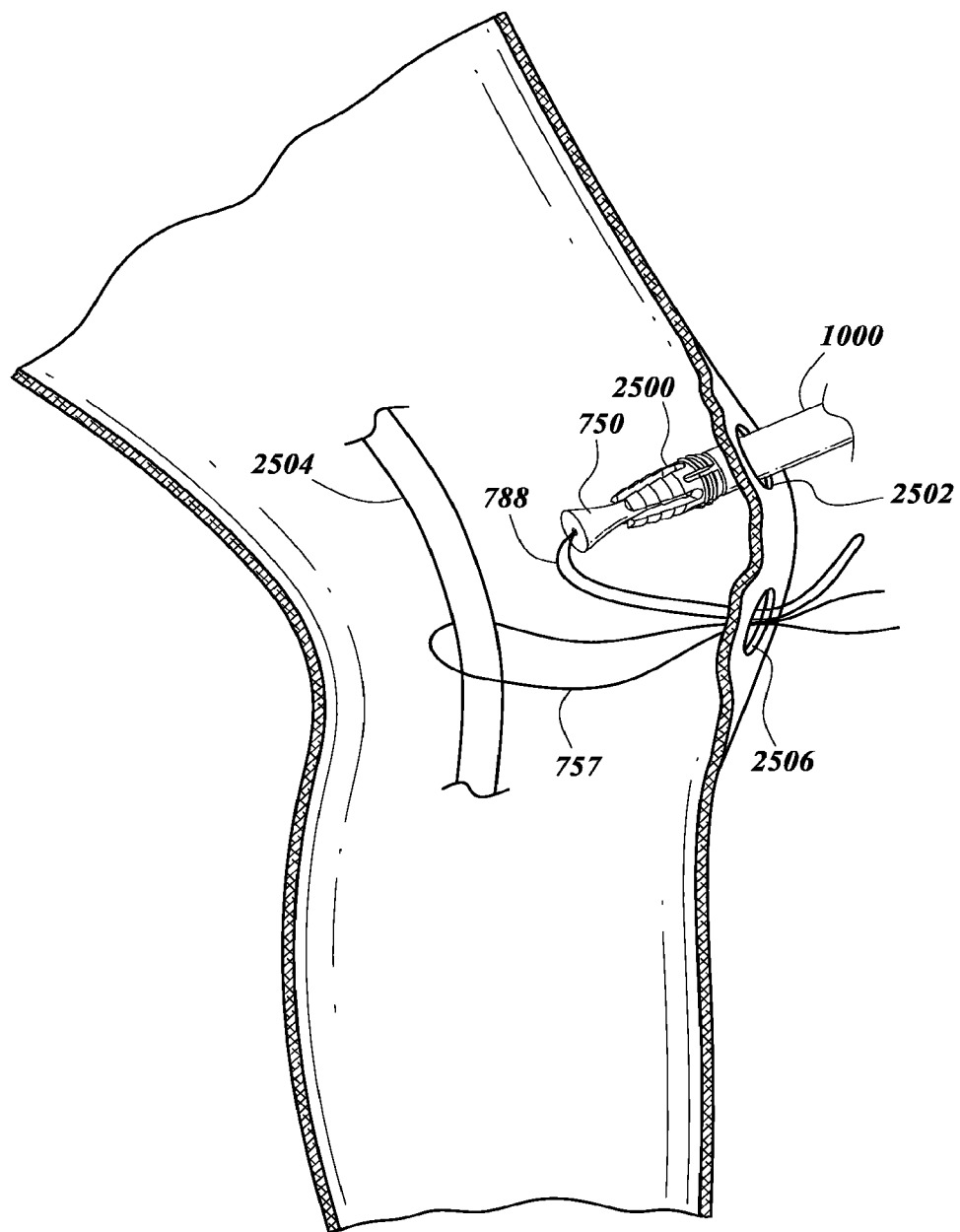
Figure 19D:
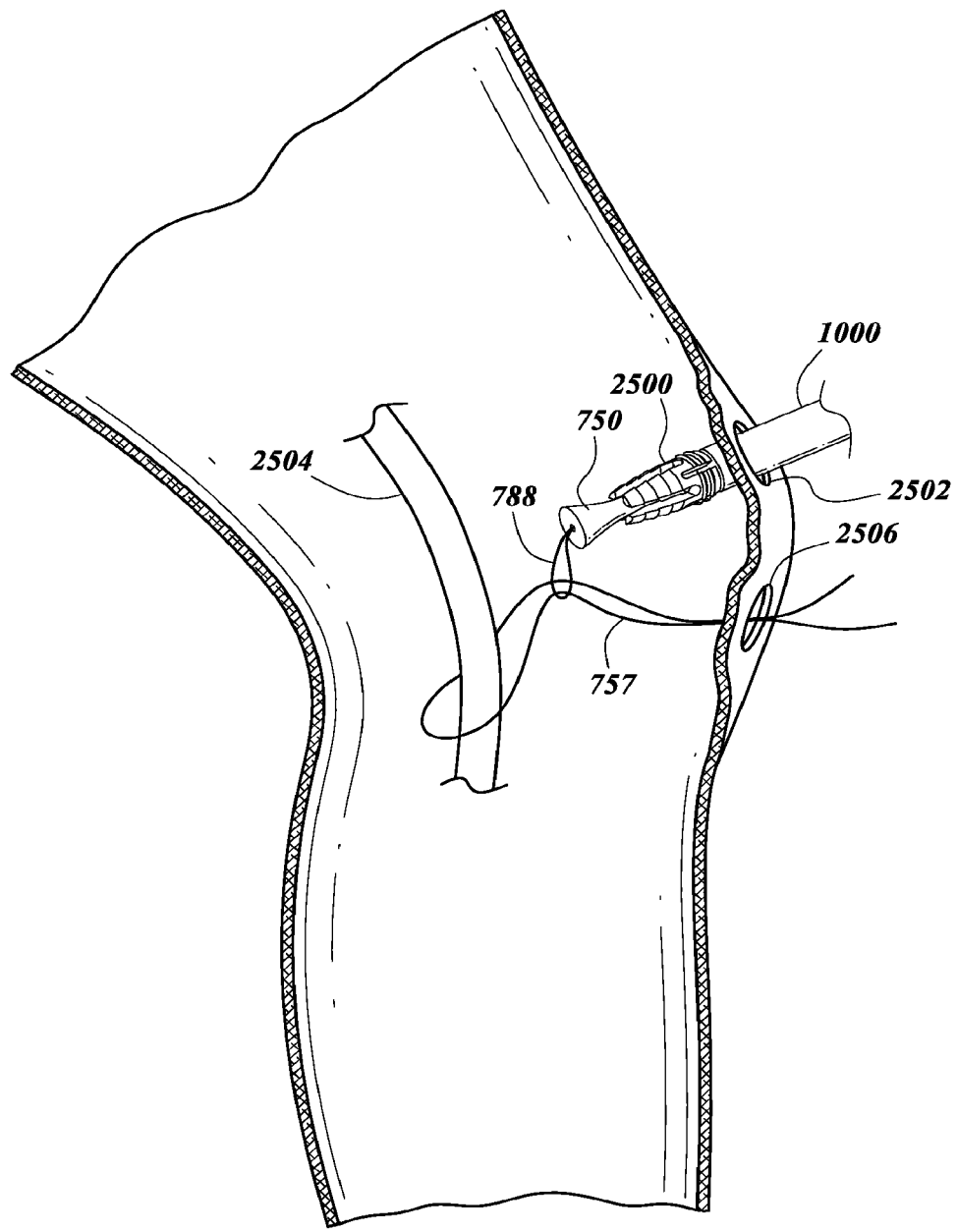
Figure 19E:
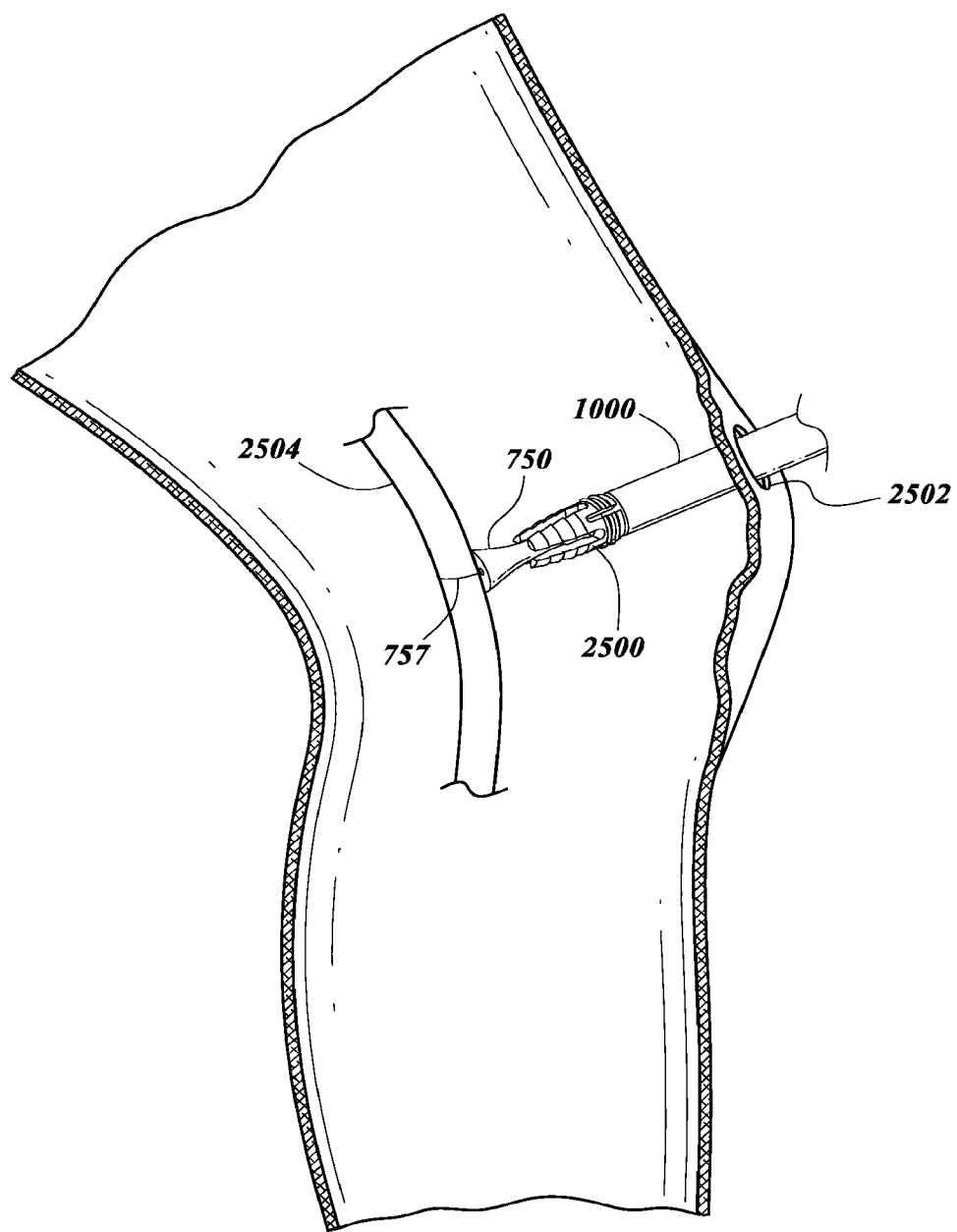

FIGS. 19A through 19E depict an additional method of securing soft tissue to an anchor 2500. As depicted in FIG. 19A, the anchor 2500 comprises an expander 750 including a wire loop 788. The wire loop 788 extends from the anchor through a first hole on the distal end of the anchor expander 750. The ends of the wire loop 788 may extend proximally through the interior of the anchor 2500 and the interior of the inserter tool 1000 to a position where they can be held and manipulated by a surgeon. As depicted in FIG. 19A, the anchor 2500 is inserted through the first arthroscopic port 2502 to a position proximate to, for example, the tendon 2504. After the anchor 2500 is positioned proximate to the tendon 2504, the process then proceeds to FIG. 19B and a suture 757 is passed through the second arthroscopic port 2506 and passed around the tendon 2504. The passing of the suture 757 through the second arthroscopic port 2506 can be performed using any of a number of tools and techniques. After the suture 757 is passed around the tendon 2504, the process proceeds to FIG. 19C, and the wire loop 788 is pulled through the second arthroscopic port 2506. After the wire loop 788 is pulled through the second arthroscopic port 2506, the suture 757 can be passed through the wire loop 788. In some embodiments, a sufficiently length of suture 757 is passed through the wire loop 788 to allow the wire loop 788 to reliably retract the suture 757 through the second arthroscopic port 2506 and through the anchor 2500 and the inserter tool 1000. After the suture 757 is passed through the wire loop 788, the process proceeds to FIG. 19D, in which the wire loop 788 may be retracted (e.g., by pulling on the ends of the wire that extend through the anchor inserter 1000) down through the second arthroscopic port 2506. As seen in FIG. 19D, the retraction of the wire loop 788 through the second arthroscopic port 2506 likewise retracts a portion of the suture 757 through the second arthroscopic port 2506. Next, the wire loop 788 can further be retracted (e.g., by pulling on the ends of the wire that extend through the anchor inserter 1000) through the interior of the expander 750, the interior of the anchor 2500, and the interior of the inserter tool 1000, and out of the patient's body in the vicinity of the inserter 1000. Advantageously, the retraction of the wire loop 788 through these features can likewise retract the limb of the suture 757 that extends through the port 2506 through these features. After the wire loop 788 is retracted, pulling the suture 757 with it, the process moves to FIG. 19E and the tendon 2504 is secured to the anchor 2500 by the suture 757, which forms a loop around the tendon 2504 with its two suture limbs extending through the interior of the anchor 2500 and the interior of the inserter 1000. In some embodiments, the tendon may be temporarily and adjustably secured to the anchor by creating tension on the two suture limbs. This tension may be manually created by a surgeon pulling on the suture limbs or the suture limbs may be secured to a portion of the inserter 1000, such as suture cleats located on a handle of the inserter 1000.

Anchor Inserter Tool

FIG. 7 depicts individual components of one embodiment of an inserter tool. An inserter tool comprises a range of features configured to allow the inserter tool to insert an anchor and then deployingly interact with the anchor. One embodiment of an inserter tool may be configured for use with a specific anchor configuration, or with a specific spreader configuration. FIG. 10 depicts an embodiment of an inserter configured for use with a single piece expander. The inserter tool comprises an inner rod or tube 1100, an outer tube 1200, a handle body 1300, a threaded actuator shaft 1400, and a deployment knob 1500. In some embodiments, the inserter 1000 is coupled to the anchor during manufacturing. In a preferred embodiment, the inserter tool is disposable.

The inserter tool 1000 is designed to insert and manipulate an anchor such as the anchor described in FIGS. 1 through 3. In some embodiments, the anchor is manufactured to be attached to an inserter tool before packaging. In other embodiments, the tissue capture anchor is coupled to the inserter tool prior to insertion. In a basic configuration, the inserter tool is assembled as follows: the inserter tool 1000 is configured such that the inner rod 1100 is disposed within the outer tube 1200. The outer tube is configured to fit against the proximal end of the anchor. The inner rod 1100 extends through outer tube 1200 and is configured to attach to the expander via threading on both the proximal hole in the expander and threading on the distal end of the inner rod 1100. The proximal end of the outer tube 1200 is connected to a handle 1300 and the inner rod 1100 extends through the proximal end of the outer tube 1200 and screws into the threaded actuator shaft 1400. The actuator shaft 1400 extends just past the proximal end of the handle 1300 where it is configured to secure with a deployment knob 1500.

The individual components of the inserter tool are further described in detail below.

Figure 7A:
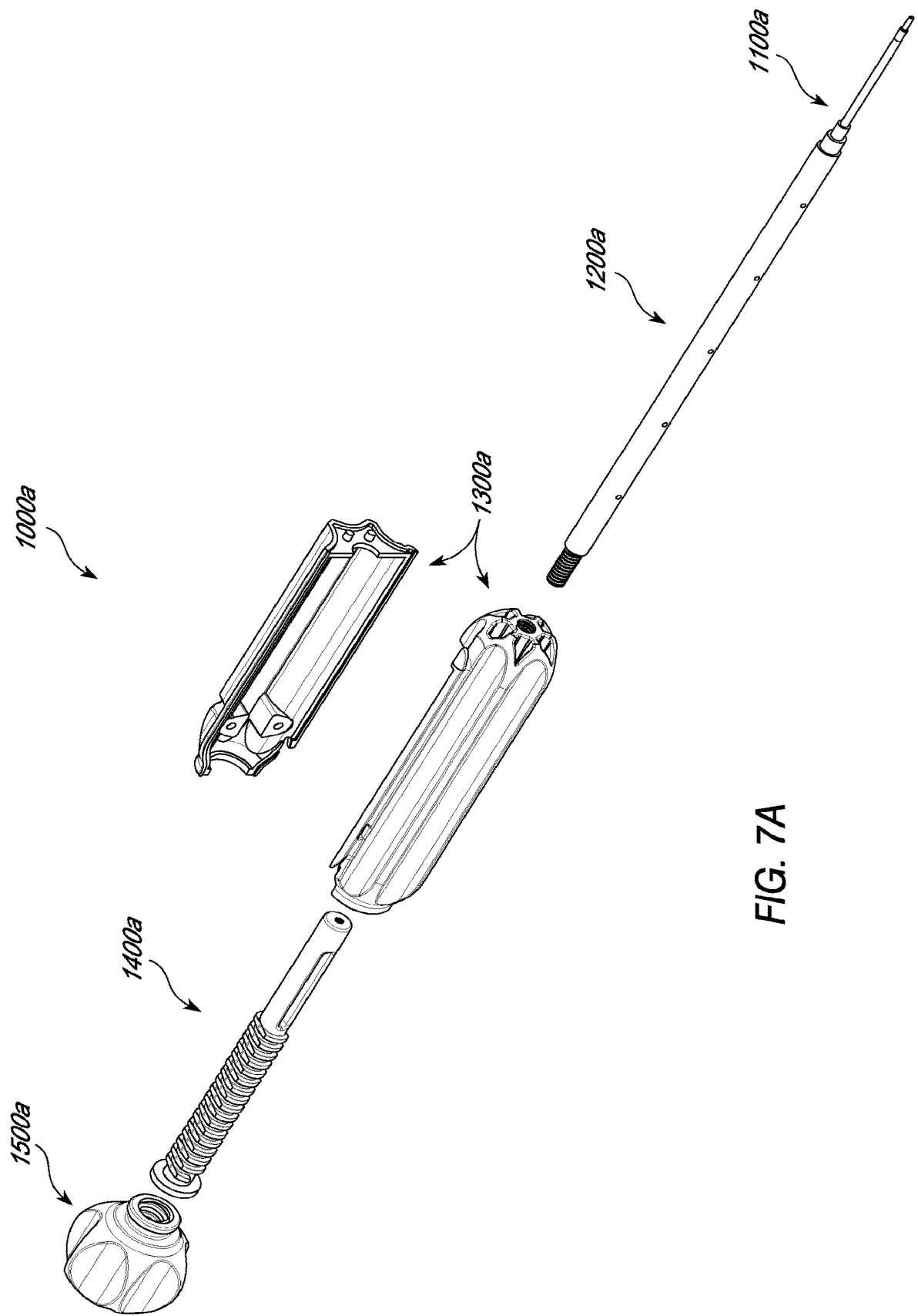
FIG. 7A depicts an exploded perspective view of one embodiment of an inserter tool configured for use with a two piece expander.

FIG. 7A depicts an embodiment of an inserter configured for use with a two piece expander. Like the inserter tool 1000 depicted in FIG. 7, inserter tool 1000a comprises an inner rod or tube 1100a, an outer tube 1200a, a handle body 1300a, a threaded actuator shaft 1400a, and a deployment knob 1500a. In some embodiments, the inner rod or tube 1100a, the outer tube 1200a, the handle body 1300a, the threaded actuator shaft 1400a, and the deployment knob 1500a of inserter tool 1000a can fit together as described in relation to those features of FIG. 7. In some embodiments, some or all of the inner rod or tube 1100a, the outer tube 1200a, the handle body 1300a, the threaded actuator shaft 1400a, and the deployment knob 1500a of inserter tool 1000a can include additional features configured to facilitate use with a two piece expander. These differences can include, for example, additional features located on the outer tube 1200a, or on any other feature of the inserter tool 100a. Additional features of the outer tube 1200a will be discussed in greater detail below.

Figure 8:
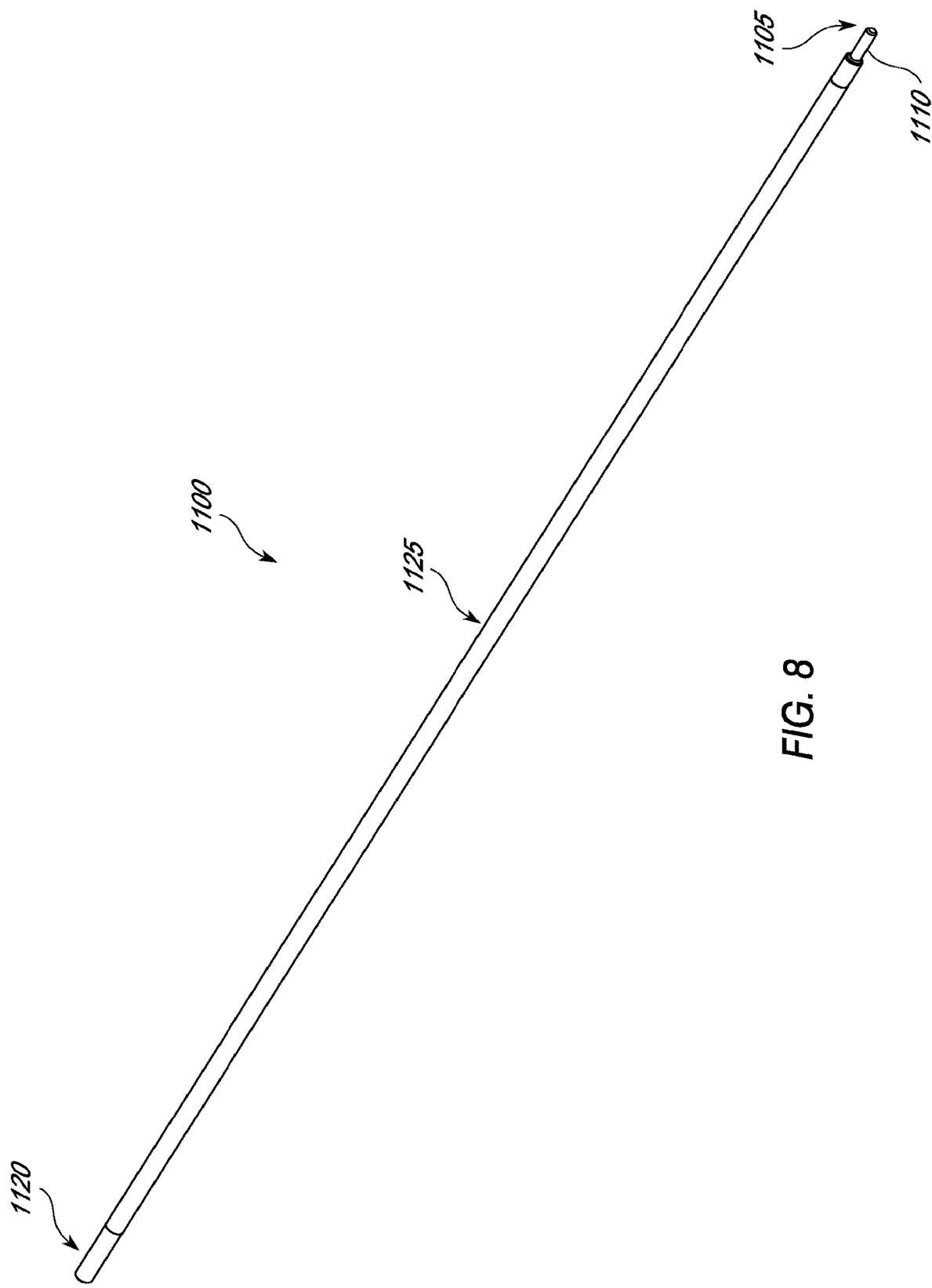
FIG. 8 is a perspective view of one embodiment of an inner rod.

FIG. 8 shows a perspective view of an embodiment of the inner rod 1100. In some embodiments, the inner rod is an inner tube. The inner rod comprises a distal end configured to secure to the expander, a proximal end which is configured to interact with the other components of the inserter, for instance the actuator shaft 1400. The inner rod 1100 is configured that a proximal end 1120 is advanced through the outer tube 1200 and into the handle 1300 where it is further secured within the actuator shaft 1400 via threading. The distal end 1105 of the inner rod 1100 is configured to be advanced through the central hole in the anchor body and then secured to the expander until the anchor is fully deployed and the inner rod 1100 is separated from the anchor. In some embodiments, the distal end 1106 can comprise features configured to engage with the expander, such as, for example, threads 1110. The body 1125 of the inner rod 1100 is configured for sliding positioning within outer tube 1200.

The inner rod 1100 extends through the central hole in the anchor body before coupling with the expander. In one embodiment, the inner rod 1100 couples with the expander through threads on the end of the inner rod 1100 and within the proximal end of the expander. In other embodiments, the inner rod 1100 may couple to the expander through other securing mechanisms such as adhesives, welding or frictional fit.

Figure 9:
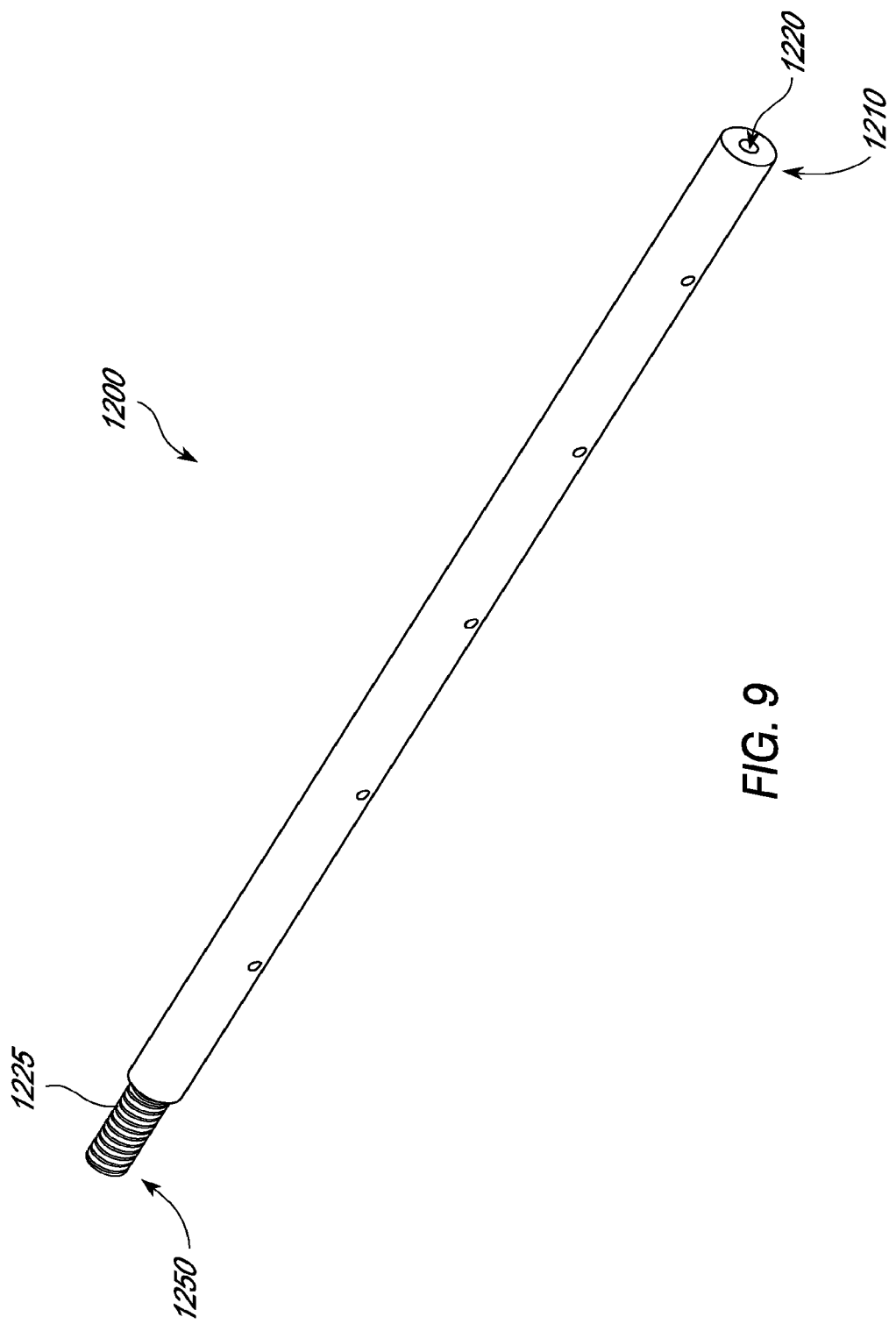
FIG. 9 is a perspective view of one embodiment of an outer rod.

FIG. 9 shows an embodiment of the outer tube 1200. The outer tube 1200 is attached at its proximal end 1205 to the distal end of handle via threading 1225. The distal end 1210 of the outer tube 1200 is configured such that the inner rod is drawn into the outer tube 1200 and through opening 1220 in the distal end 1210 of outer tube 1200 where it is secured to the expander. When the inner tube is advanced far enough that the expander locks into place or cannot advance anymore, the outer tube 1200 distal surface is surface-to-surface with the proximal surface of the anchor body. When the inner rod withdraws further into the outer tube upon the continued rotation of the deployment knob and advancement of the actuator shaft, the inner rod strips the threading from the expander and the inserter tool detaches from the anchor.

Figure 9A:
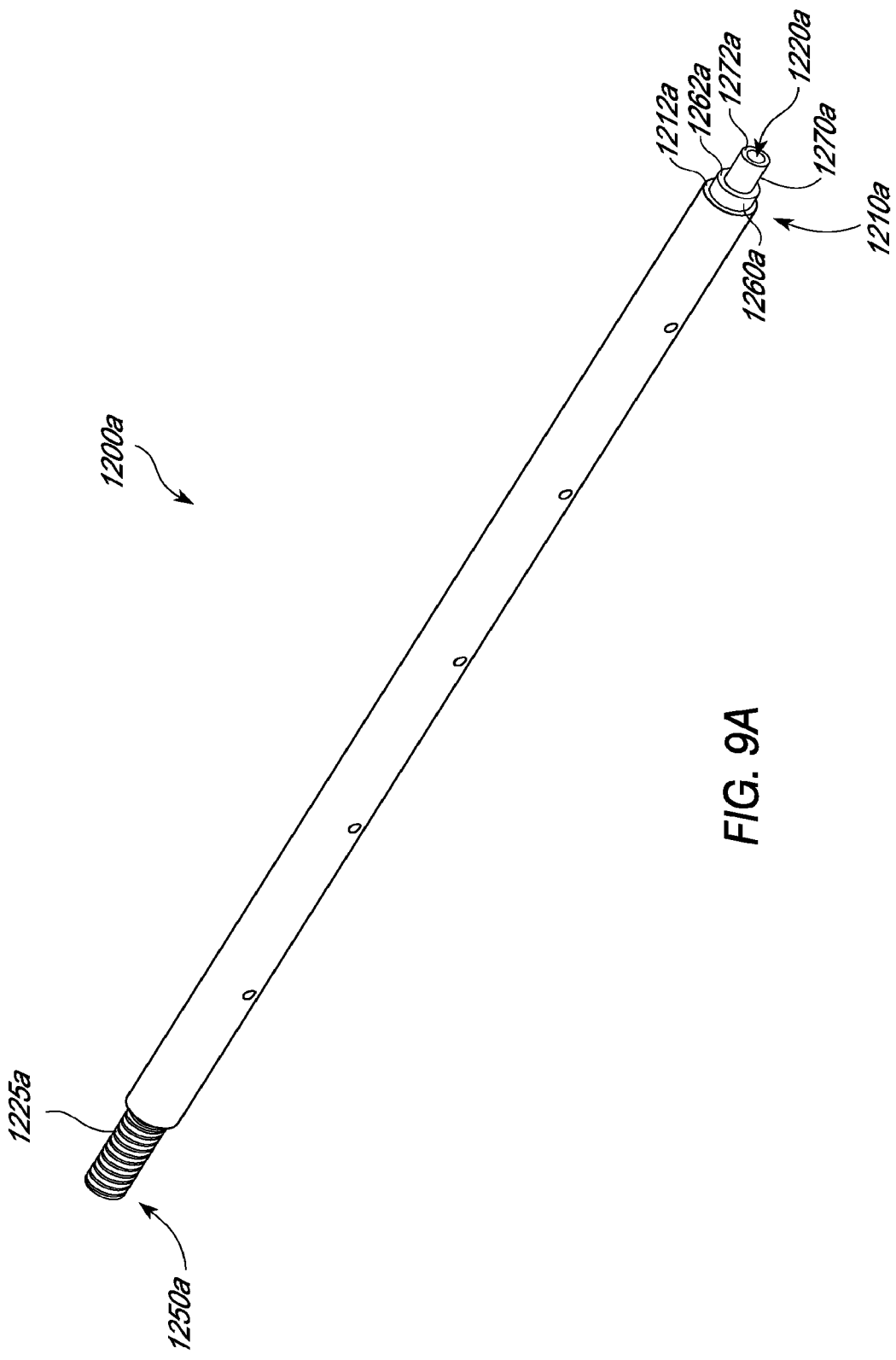
FIG. 9A is a perspective view of one embodiment of an outer rod configured for use with a two piece expander.

FIG. 9A shows an embodiment of the outer tube 1200a configured for use with a two piece expander. The outer tube 1200a is attached at its proximal end 1205a to the distal end of handle via threading 1225a. The distal end 1210a of the outer tube 1200a is configured such that the inner rod is drawn into the outer tube 1200a and through opening 1220a of the distal end 1210a of outer tube 1200a where it is secured to the expander. In some embodiments of an outer tube 1200a configured for use with a two piece expander, the distal end 1210a of the outer tube comprises a first abutment 1212a. In some embodiments, the first abutment 1212a is configured for abutting engagement with the second end 114, 414 of a dual expansion anchor 100, 400.

In some embodiments, the distal end 1210a of the outer tube 1200a comprises a first base 1260a and a first elevated abutment 1262a. In some embodiments, the first base 1260 is sized and dimensioned to fit within portions of the axial bore 116, 416 proximate to the second end 114, 414 of anchor 100, 400. The first base 1260a can be, for example, sized and shaped to slidably enter portions of the axial bore 116, 416 proximate to the second end 114, 414 of the dual expansion anchor 100, 400 when the dual expansion anchor 100, 400 is in its deployed or expanded configuration, or, alternatively, to slidably enter portions of the axial bore 116, 416 proximate to the second end 114, 414 of the dual expansion anchor 100, 400 when the dual expansion anchor 100, 400 is in its undeployed or unexpanded configuration. In some embodiments, the first elevated abutment 1262a of the outer tube 1200a is configured for abutting engagement with the second end 922 of the second expansion member 904.

In some embodiments, the distal end 1210a of the outer tube 1200a comprises a second base 1270a and a second elevated abutment 1272a. In some embodiments, the second base 1270a is sized and dimensioned to fit within portions of the axial bore 116, 416 proximate to the second end 114, 414 of anchor 100, 400. In some embodiments, second base 1270a is configured to slidingly extend through a thru-hole in the second expansion member 904. In some embodiments, the second base 1270a can be sized and configured to extend through the second expansion member 904. In some embodiments, the second base 1270a terminates at a point within the axial bore 116, 416 of the anchor 100, 400 where the second elevated abutment 1272a abuts the second end 912 of the first expansion member 902 when the dual expansion anchor is in its deployed or expanded configuration.

In some embodiments, the features of the distal end 1210a of the outer tube 1200a are configured to facilitate deployment of a dual expansion anchor 100, 400 with a two piece expander 900. In some embodiments, a dual expansion anchor 100, 400 can be positioned on the distal end 1210 of the outer tube 1200a of an inserter tool 1000a. Specifically, in some embodiments, the second expansion member 904 of a dual expansion anchor 100, 400 can abut the first elevated abutment 1262a. In some embodiments, the second base 1270a and the inner tube 1100a can extend through a thru-hole in the second expansion member 904 of a dual expansion anchor 900. In some embodiments, a second end 114, 414 of the anchor body 110, 410 can contact the second expansion member 904 of the two piece expander 900 and the first end 112, 412 of the dual expansion anchor 100, 400 can contact the first expansion member 902 of the two piece expander 900. In some embodiments the first expansion member 902 of the two piece expander 900 can be affixed to the inner tube 1100a. When the inner tube 1100a is longitudinally displaced to expand/deploy the anchor 100, 400, the inner tube 1100a applies a force to the first expansion member 902 of the two piece expander 900 while the first elevated abutment 1262a applies a reactionary force to the second expansion member 904 of the two piece expander 900. The application of these forces can displace the first and second expansion members 902, 904 of the two piece expander 900 until both the first and second expansion members 902, 904 of the two piece expander 900 are in their deployed position. More specifically, the first expansion member 902 of the two piece expander 900 can displace under applied forces until the first expansion member 902 of the two piece expander 900 contacts the second elevated abutment 1272a. Additionally, the second expansion member 902 of the two piece expander 900 can displace under the applied forces until second end 114, 414 of the anchor body 110, 410 contacts the first abutment 1212a of the distal end 1210a of the outer tube 1200a. In some embodiments, the second elevated abutment 1272a can be positioned relative to the first elevated abutment 1262a, and the dual expansion anchor 100, 400 can be designed such that the first expansion member 902 of the two piece expander 900 only contacts the second elevated abutment 1272a after the second end 114, 414 of the anchor body 110, 410 contacts the first abutment 1212a of distal end 1210a of the outer tube 1200a. After both the first and second expansion members 902, 904 of the two piece expander 900 reach their deployed/expanded positions, the inner tube 1100a is separated from the first expansion member 902 of the two piece expander 900, and the connection between the inserter tool 1000a and the anchor 100, 400 is terminated.

Figure 10A:
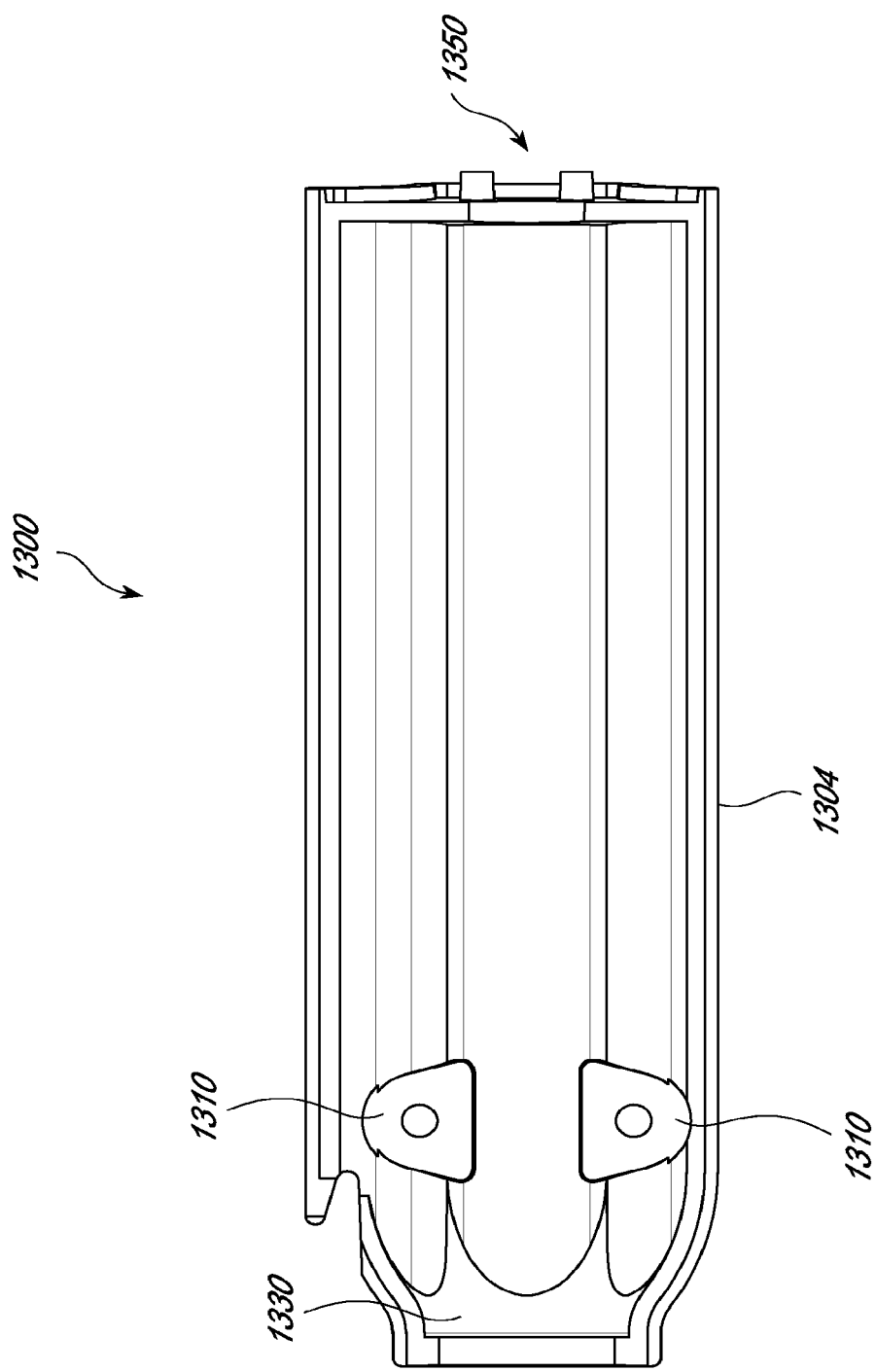
FIG. 10A is a side view of one embodiment of a portion of a handle body.
Figure 10B:
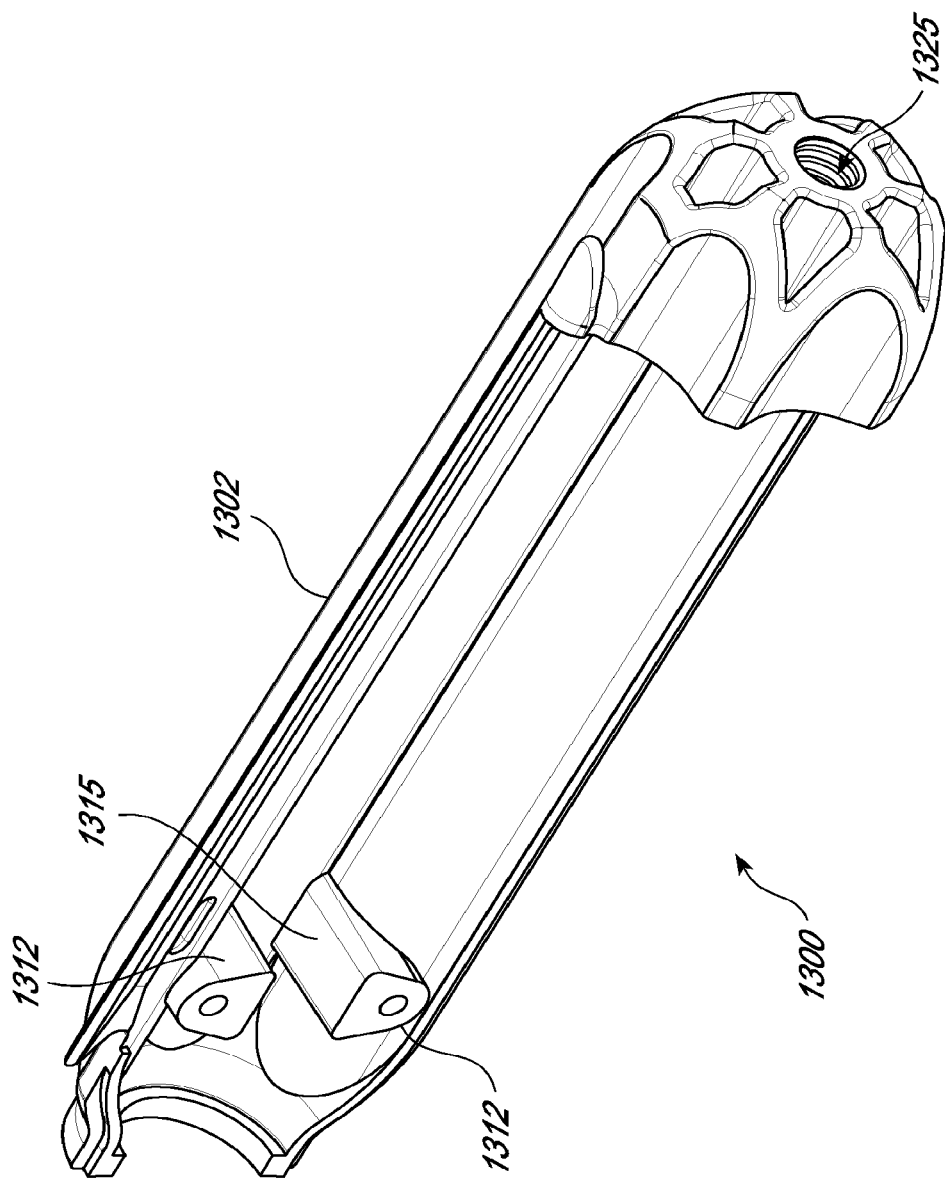
FIG. 10B is a perspective view of one embodiment of a portion of a handle body.

FIGS. 10A and 10B show embodiments of a handle body 1300. A handle body 1300 can comprise a handle piece 1302 and a lid piece 1304. FIG. 10A is a side view of a lid piece 1304 of the handle body 1300. The proximal end of the handle 1300 is configured to receive the deployment knob via the ridges 1330 which hold the knob secure. The actuator shaft is housed within the handle body 1300. A set of flat brackets or braces 1310 secure the actuator shaft within the handle 1300. The distal end of the handle 1300 is configured to receive the outer tube via threads at opening 1350. The outer tube is permanently affixed to the handle 1300 at its distal end.

FIG. 10B depicts a perspective view of one embodiment of the handle portion 1302 of a handle 1300. Handle portion 1302 includes a threaded hole for threading engagement with threading 1225 of the outer tube 1200. Handle portion 1302 depicted in FIG. 10B further includes brace receiving openings 1312. Handle portion 1302 additionally includes flat surfaces 1315.

Figure 11:
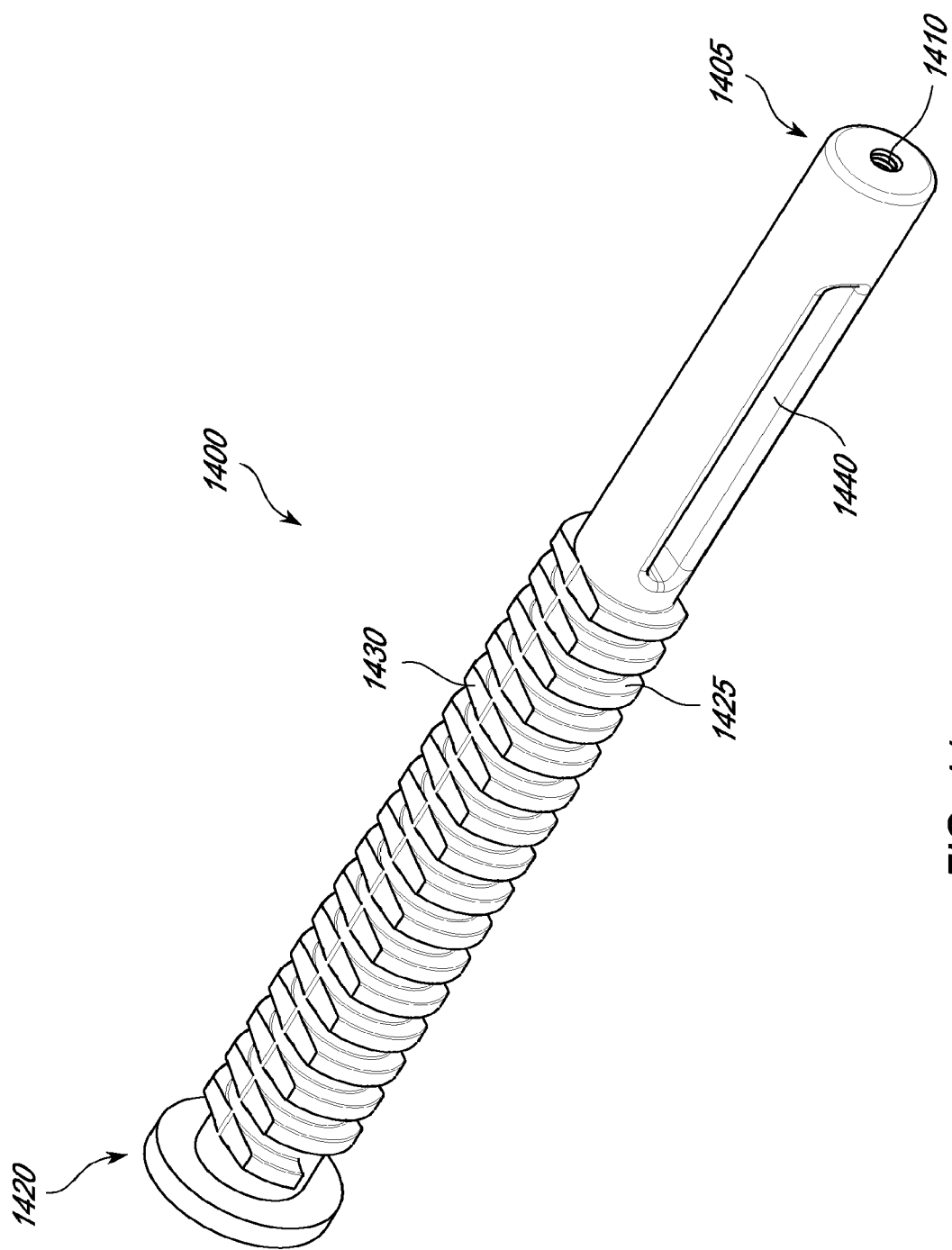
FIG. 11 is a perspective view of one embodiment of a threaded actuator shaft.

FIG. 11 depicts the threaded actuator shaft 1400. The actuator shaft 1400 is comprised of a distal end 1405 comprising a threaded hole 1410 which is configured to receive the inner rod 1100, a second threaded portion 1425 on the body of the shaft configured to advance the inner rod 1100, and a proximal end 1420 configured to secure within the deployment knob 1500. The threading 1425 of the actuator 1400 has two flat areas 1430, one on each side, where there is no threading. These flat areas 1430 fit within the flat surfaces 1315 of the handle 1300 such that the actuator 1400 cannot rotate within the handle.

The body of the actuator shaft 1400 is configured with threading 1425 to permit the shaft 1400 to advance the inner tube 1100. The body of the actuator shaft 1400 is not perfectly round, but rather is oval shaped with flat sides 1430 that are fit into the handle body 1300 in such a way that the actuator shaft 1400 cannot itself rotate when the deployment knob 1500 is turned and the shaft 1400 advances via knob 1500. Thus, the threads do not go all the way around the shaft but rather flatten out on the flattened sides of the shaft. The actuator shaft is configured as a coaxial system. That is, the expander, inner tube 1100 and actuator 1400 are configured to operate as one piece. The flat surfaces 1315 in the handle make the actuator shaft 1400 stay on plane such that the actuator shaft 1400 itself cannot rotate within the handle 1300. The proximal end of the inner tube 1100 couples with the distal end of the actuator shaft 1400 via threading.

Figure 12:
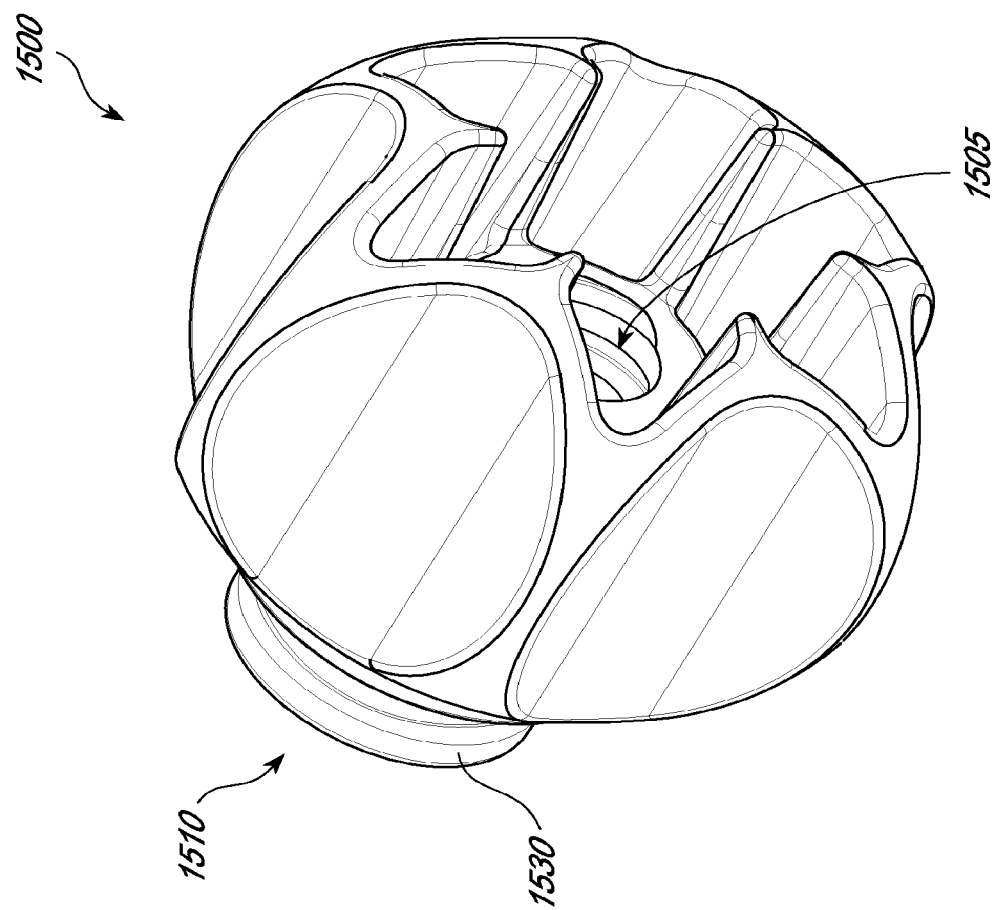
FIG. 12 is a perspective view of one embodiment of a deployment knob.

Moving to FIG. 12, a deployment knob 1500 is shown. The deployment knob 1500 comprises a central hole 1510 which is configured with threading 1505, and a groove 1530 configured to be received by a corresponding ridge 1330 of the handle 1300. The threading 1505 in the central hole 1510 is configured to receive the actuator shaft 1400. The deployment knob 1500 is configured to advance, relative to the deployment knob 1500, the inner rod 1100 via the actuator shaft 1400. The actuator shaft 1400 is joined at its proximal end to the distal end of the deployment knob 1500 via threading 1505 in the central hole 1510. The actuator shaft 1400 is attached to the inner rod 1100 by way of the proximal end of the inner rod 1100 advancing into the distal end of the actuator shaft via threading so that when the deployment knob 1500 is rotated, the mechanism of the shaft 1400 advances the inner rod 1100 proximally such that the expander is then advanced into the anchor body to expand the anchor body into bone and secure the anchor.

In one embodiment, the deployment knob 1500 is threaded 1505 to receive the actuator shaft via the groove 1530 of knob 1500 fitting with the proximal end ridge 1330 of the handle body 1300 As the deployment handle is turned, the actuator shaft 1400 is advanced in a proximal direction until the anchor body is deployed and locked into place.

Figure 13A:
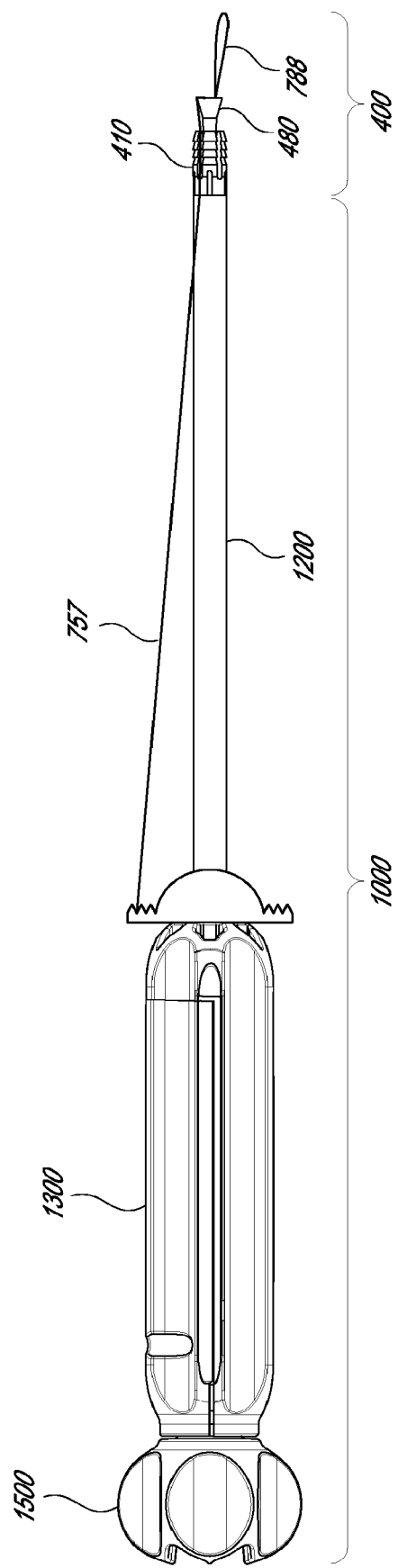
FIG. 13A depicts a side view of one embodiment of an inserter with an attached anchor, a wire loop, and a suture.

FIG. 13A shows one embodiment of a dual expansion anchor 400 coupled to the inserter tool 1000. The anchor 400 comprises the anchor body 410 and the expander 480. As seen in FIG. 13A, the expander 480 comprises a wire loop 788 and a suture 757. As further seen in FIG. 13A, the inserter tool 1000 includes a cleat 1450. In some embodiments, the inserter tool 1000 can comprise one or several cleats 1450, which can be located, for example, on any desired portion of the inserter tool 1000. In some embodiments, the cleat 1450 can be configured to facilitate in securing the suture 757, and specifically, the cleat 1450 can be used to secure one or both ends of the suture 757. In one specific embodiment, the inserter tool 1000 can comprise a first cleat located on the side of the handle body 1300, and a second cleat can be located at a position on the handle body 1300 between the handle body 1300 and the outer tube 1200. In such an embodiment, the first cleat can secure a first end of the suture 757 and the second cleat can secure a second end of the suture 757. A person of skill in the art will recognize that any of the above disclosed, or other features configured for engaging with and capturing material to be secured to the bone can be used in connection with a dual expansion anchor 400 coupled to an inserter tool 1000.

The inserter tool 1000, as shown, includes the outer tube 1200, the handle 1300 and the deployment knob 1500. The inner rod 1100 is positioned within the outer tube 1200, and the outer tube is flush with the anchor body 410. The outer tube 1200 may hold the anchor body 410 steady during insertion and deployment. The inner rod 1100 extends through the anchor body 410 and couples with the expander 480 via threading. The expander 480 is configured to be advanced through the distal end of the anchor body 410 by the inner rod 1100 via a rotating the deployment knob 1500.

In another embodiment, the inner rod 1100 extends through the expander 480. The inner rod 1100 is configured with a sharp, pointed tip such that the tip of the inner rod 1100 spears or captures tissue to secure into the bone hole before the anchor body 410 is fully deployed.

The inner rod 1100 provides the mechanism to draw the expander 480 into the central bore 416 in the anchor body 410 to fully expand the anchor body 410. During deployment of the tissue capture anchor 400, the inner rod 1100 is continually advanced via a screwing motion until the expander locks with the anchor body. As the deployment knob 1500 continues to turn and the inner rod 1100 continues to pull on the threads of the expander 480, the inner rod 1100 strips the threads from the inside of the expander 480 and the insertion tool 1000 releases from the anchor body 410. Any thread shavings are contained within the outer tube 1200.

Figure 14:
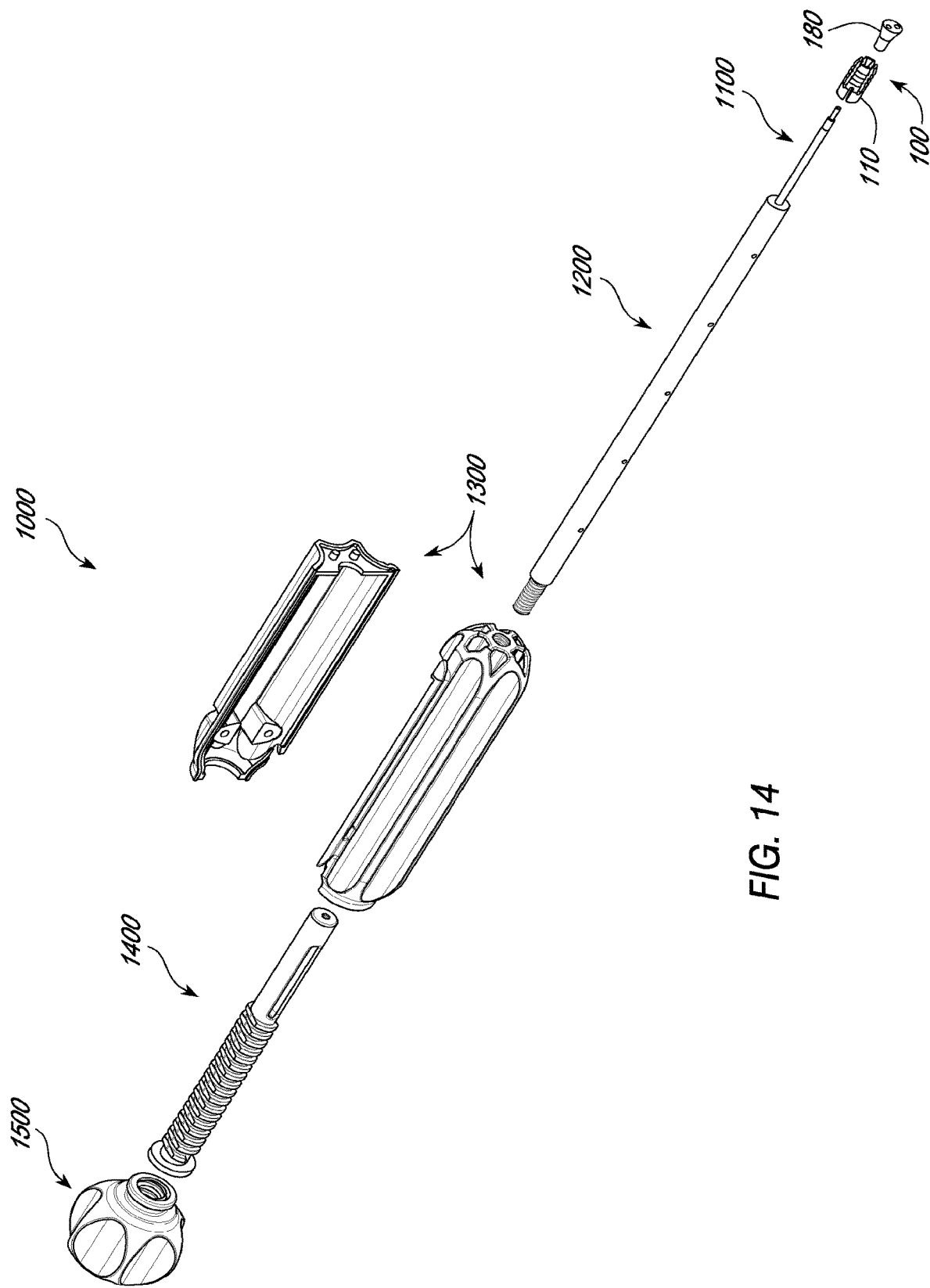
FIG. 14 depicts an exploded view of one embodiment of an inserter and anchor.

FIG. 14 illustrates an exploded view of the anchor 100 and the inserter 1000. The tissue capture anchor 100 comprises the anchor body 110 and the expander 180. The inserter tool 1000, as shown, includes the outer tube 1200, the handle 1300 and the deployment knob 1500. The inner rod 1100 is positioned within the outer tube 1200, and the outer tube is flush with the anchor body 110. The outer tube 1200 may hold the anchor body 110 steady during insertion and deployment. The inner rod 1100 extends through the anchor body 110 and couples with the expander 180 via threading. The expander 180 is configured to be advanced through the distal end of the anchor body 110 by the inner rod 1100 via a rotating the deployment knob 1500.

The inner rod 1100 provides the mechanism to draw the expander 180 into the central hole in the anchor body 110 to fully expand the anchor body 110. During deployment of the tissue capture anchor 100, the inner rod 1100 is continually advanced via a screwing motion until the expander locks with the anchor body. As the deployment knob 1500 continues to turn and the inner rod 1100 continues to pull on the threads of the expander 180, the inner rod 1100 strips the threads from the inside of the expander 180 and the insertion tool 1000 releases from the anchor body 110. Any thread shavings are contained within the outer tube 1200.

In some embodiments, a pre-attached delivery handle is provided. In some embodiments, the insertion tool or delivery handle is disposable. In other embodiments, the insertion tool can be sterilized, reloaded and reused.

Those of skill in the art will appreciate other inserters and mechanisms that may be used to insert and deploy the dual expansion anchor 100,400 described herein.

Although a particular inserter device for inserting and manipulating dual expansion anchor 100,400 has been described, it should be understood that other inserter designs may be used for manipulating the parts of dual expansion anchor 100,400 described above to insert the anchor into bone and tissue to the bone. For example, it may be possible to use separate tools for inserting the anchor and deploying the anchor.

It will be appreciated that there are numerous combinations of anchors and their placement that may be used to secure soft tissue to bone by the methods and devices described herein. These variations as well as variations in the design of the above described anchor devices and inserter devices are within the scope of the present disclosure.

Methods of Attaching Soft Tissue to Bone

Various embodiments include methods for attaching soft tissue to bone. In some embodiments, the methods include using the tissue capture anchors described above. In one preferred embodiment, a biceps tenodesis procedure is performed arthroscopically.

The biceps tendon connects the biceps muscle to the bone. The biceps tendon connects the biceps muscle to the bone. The tendon passes from the muscle to the shoulder joint. Biceps tendon problems can also occur in conjunction with a rotator cuff tear.

A biceps tenodesis is a procedure that cuts the normal attachment of the biceps tendon on the shoulder socket and reattaches the tendon to the bone of the humerus (arm bone). By performing a biceps tenodesis, the pressure of the biceps attachment is taken off the cartilage rim of the shoulder socket (the labrum), and a portion of the biceps tendon can be surgically removed. Essentially a biceps tenodesis moves the attachment of the biceps tendon to a position that is out of the way of the shoulder joint.

A biceps tenodesis is often, but not always, performed in patients with significant biceps tendon symptoms, and evidence at the time of viewing of biceps tendon inflammation or tears.

The procedure using a tissue capture anchor described herein merely requires drilling the bone hole and capturing the tendon with the anchor and dragging the tendon into the bone hole. In some embodiments, a further advantage when using an awl to make the bone hole is that the whole procedure can be percutaneous.

Figure 15:
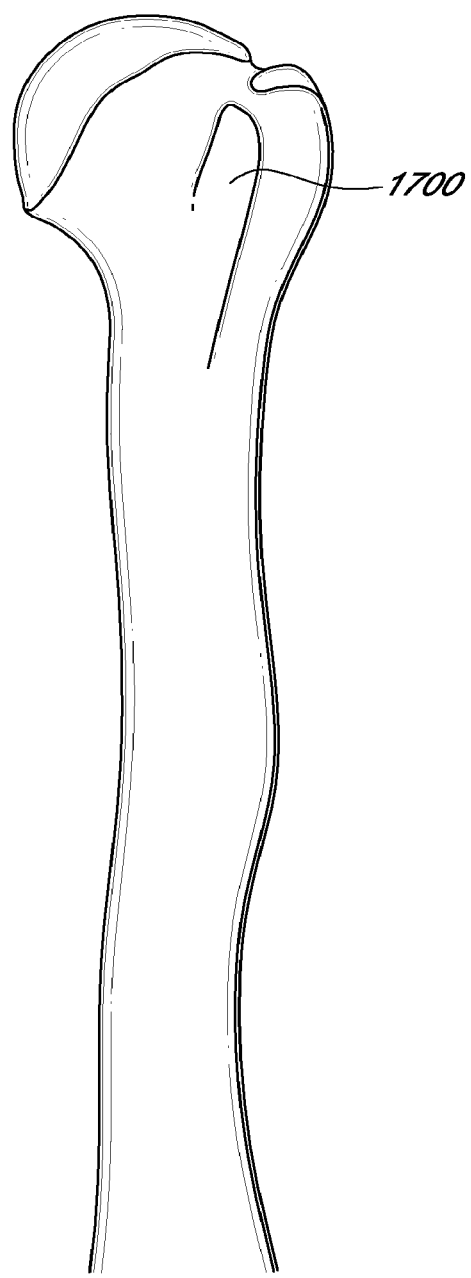
FIG. 15 depicts a bicipital groove and surrounding bone of the shoulder and biceps.
Figure 16:
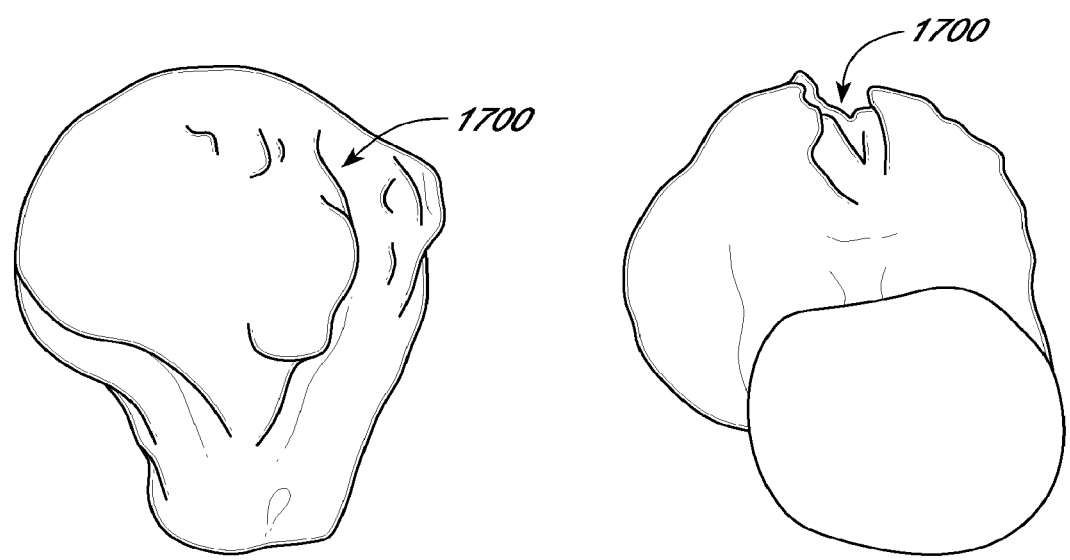
FIG. 16 depicts a bicipital groove and surrounding bone of the shoulder and biceps.

In one method, the procedure is performed arthroscopically. In one embodiment, the procedure is performed non-arthroscopically. In one embodiment, for example, a percutaneous approach may be used. In one embodiment, a 6 mm anchor is used, although different sizes and materials may be used. In some instances the hole into which the tissue capture anchor will be inserted is made by making a clearance hole for the anchor in the superior portion of the bicipital groove 1700, as shown in FIG. 15, using a drill bit or suitably sized awl. The hole may also be made in any other suitable position depending on pathology of the tendon, etc. FIGS. 15 and 16 show different views of the bicipital groove and surrounding bone of the shoulder and biceps. The bicipital groove is a furrow on the upper part of the humerus occupied by the long head of the biceps and is also called the intertubercular groove. In some embodiments a 7 mm drill bit is used; however in other embodiments, a different sized drill bit can be used. In one embodiment, the clearance hole can range from 5 mm wide to 9 mm wide, from 6.5 mm to 8 mm wide, or any other desired range. In other embodiments, the size of the clearance hole will vary, as the size depends on the size of the anchor. Depending on the softness of the bone and the size of the anchor, the hole can be from 8 mm-40 mm deep, approximately 21 mm deep, approximately 30 mm deep, or any other desired depth. For example, in one embodiment, a 6 mm tissue capture anchor is used, and for soft bone, the hole can be at least 11 mm deep. For average bone, the hole can be approximately 10-12 mm deep. For very soft bone, the hole can be approximately 20 mm.

The implantation site is cleared of any soft tissue in the region of the bone hole using a bur or other suitable means. Angled protrusions or teeth may be used that provide greater resistance to removal of the anchor body 110, 410 than to insertion.

In one nonlimiting embodiment, the shoulder preparation is as that used by Richards and Brukhart ("A Biomechanical Analysis of Two Biceps Tenodesis Fixation Techniques" Arthroscopy. The Journal OF Arthroscopic and Related Surgery Vol 21, No 7 (July), 2005: pp 861-866) which is incorporated by herein by reference in its entirety. The shoulder will undergo soft tissue dissection to the level of the rotator cuff. At this point, the supraspinatus tendon insertion is reflected by sharp dissection and the long head biceps tendon inspected for any evidence of pathology. The tendon of the LHB is then sharply incised, freeing from its intra-articular origin at the superior aspect of the glenoid as well as dividing it as the musculotendinous junction so that the biceps tendon is a free segment. In other embodiments, other methods of shoulder preparation are used.

In some exemplary embodiments, repairs are complete by drilling a clearance hole for the anchor in the superior portion of the bicipital groove using a standard drill bit. The tendon will then be captured by the anchor as described above and forced in to the clearance hole and the anchor placed to capture the tendon. The tendon will be essentially folded around the anchor longitudinally, resulting in a double surface contact. The proximal surface of the anchor will be situated flush with the cortical surface. In some embodiments, the hole can be located in other portions of the bone. In one exemplary embodiment, the hole may be placed, approximately, 1 cm distal to the end of the bicipital groove.

In another embodiment, anchors as described above are used for anterior cruciate ligament (ACL) repair. In this embodiment, a femoral tunnel is drilled in the bone. One or two bundles of hamstring tendon are captured by the anchor. The anchor is then inserted into the bone and deployed as discussed above. As described above, the tendon may be captured using a variety of methods.

In one embodiment, a hole is drilled in to the bone at a diameter of about 9 mm. The anchor is positioned such that a grasper tool can be implemented to grasp a tendon. The tendon can then be manipulated and moved or positioned. In one embodiment, a double bundle of tendons is inserted into a single bone tunnel in the femur. In one embodiment, a gracilis and a semitendinosus tendon are both doubled over for insertion into the bone hole. The anchor, which, in one embodiment may be about 8 mm or 9 mm in diameter, is inserted into the bone hole with the doubled over tendons. Due to the size of the hole, the anchor, which may be 8 or 9 mm in diameter is inserted with the doubled over tendons draped over its tip into the hole. The anchor is also suited for single bundle single tunnel and single bundle double tunnel procedures. In other embodiments, the bone hole and the anchor can be difference sizes as needed.

In one embodiment, the surgeon drills through the tibia and up into the femur and loads the anchor plus tendons through the tibial tunnel. In one embodiment, an anteromedial portal is used to drill the femoral tunnel and a separate tibial tunnel.

It will be appreciated by those of skill in the art that the tissue capture anchor 400 and 2500 and inserter tool 1000 provide a system for easy attachment of a tendon or tissue to bone. The anchor 400 and 2500 may be inserted into bone with minimal disruption of surrounding tissue. Only an access route having the diameter of the outer tube 1200 and the anchor body 410 is required. Furthermore, the anchor can be securely attached to the bone without having to insert additional instrumentation into the site or without performing any cumbersome attachment maneuvers such as knot tying.

In another embodiment, anchors as described above are used for other procedures in the knee such as, for example, patellofemoral ligament reconstruction, posterolateral corner reconstruction, and tibial anchor back-up for an ACL procedure.

In some embodiments, anchors as described above can be used for numerous tissue fixation procedures in foot and ankle. These include flexor hallucis longus transfer to Achilles for loss of Achilles mechanism; posterior tibial tendon to anterior midfoot (middle cuneiform) also known as bridle/modified bridle procedure for foot drop; Lateral ligament reconstruction with allograft (potentially as primary with Brostrom-Gould type procedure) for ankle instability or non-anatomic lateral ligament reconstruction using split peroneus brevis; deltoid ligament reconstruction with allograft (for deltoid insufficiency); flexor digitorum longus or flexor hallucis longus transfer to peroneal for non-reconstructable peroneal tendon tears and reconstruction of torn tibialis anterior with extensor hallucis longus tendon transfer.

The invention claimed is:

1. A bone anchor, comprising:
an expandable anchor body comprising a first end, a second end and an axial bore;
a multiple piece expander positionable within the axial bore and comprising:
a first expansion member and a separate second expansion member, wherein the first expansion member has a first expansion portion;
wherein the first expansion member is displaceable between a first position relative to the anchor body and a second position relative to the anchor body, wherein the first expansion portion is configured to expand the first end of the anchor body when the first expansion member is in the second position;
wherein the second expansion member has a second expansion portion, and wherein the second expansion member is displaceable between a third position relative to the anchor body and a fourth position relative to the anchor body, wherein the second expansion portion is configured to expand the second end of the anchor body when the second expansion member is in the fourth position.

2. The bone anchor of claim 1, wherein the first expansion portion has a first base portion defined by a first radius and a first shaft portion defined by a second radius that is smaller than the first radius.

3. The bone anchor of claim 2, wherein the second expansion portion has a second base portion defined by a third radius and a second shaft portion defined by a fourth radius that is smaller than the third radius.

4. The bone anchor of claim 3, wherein the first expansion member tapers in a first direction toward the second expansion member, and the second expansion member tapers in a second direction toward the first expansion member.

5. The bone anchor of claim 1, wherein the axial bore includes a first stop configured to prevent movement of the first expansion member toward the first end.

6. The bone anchor of claim 1, wherein the axial bore includes a second stop configured to prevent movement of the second expansion member toward the second end.

7. The bone anchor of claim 1, wherein each of the first end of the anchor body and the second end of the anchor body is expandable by pivoting from a position between the first end and the second end.

* * * * *